(12) United States Patent
Moffitt et al.

(10) Patent No.: US 11,013,912 B2
(45) Date of Patent: May 25, 2021

(54) NEUROSTIMULATION SYSTEM FOR DELIVERING SELECTIVITY MODES

(71) Applicant: Boston Scientific Neuromodulation Corporation, Valencia, CA (US)

(72) Inventors: Michael A. Moffitt, Saugus, CA (US); G. Karl Steinke, Valencia, CA (US); Richard Mustakos, Simi Valley, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 105 days.

(21) Appl. No.: 16/387,231

(22) Filed: Apr. 17, 2019

(65) Prior Publication Data

US 2019/0329025 A1    Oct. 31, 2019

Related U.S. Application Data

(60) Provisional application No. 62/663,563, filed on Apr. 27, 2018.

(51) Int. Cl.
*A61N 1/05* (2006.01)
*A61N 1/36* (2006.01)
*A61N 1/372* (2006.01)

(52) U.S. Cl.
CPC ....... *A61N 1/0534* (2013.01); *A61N 1/36067* (2013.01); *A61N 1/36178* (2013.01); *A61N 1/36175* (2013.01); *A61N 1/37247* (2013.01)

(58) Field of Classification Search
CPC .............. A61N 1/0534; A61N 1/36067; A61N 1/36178; A61N 1/36175; A61N 1/37247;
(Continued)

(56) References Cited

U.S. PATENT DOCUMENTS

| 6,516,227 B1 | 2/2003 | Meadows et al. |
| 6,560,490 B2 | 5/2003 | Grill et al. |

(Continued)

FOREIGN PATENT DOCUMENTS

WO    2014/005075 A1    1/2014

OTHER PUBLICATIONS

International Search Report and Written Opinion regarding corresponding PCT Application No. PCT/US2019/027942, dated Jul. 26, 2019.
(Continued)

*Primary Examiner* — William J Levicky
*Assistant Examiner* — Alexander M Eisenberg
(74) *Attorney, Agent, or Firm* — Lewis & Reese, PLLC

(57) ABSTRACT

Medical device systems, methods, and algorithms are disclosed for providing complex stimulation waveforms. The waveforms may selectively modulate or activate specific neural targets or selected ratios of specific neural targets. Some of the waveforms include pre-pulse phases defined by parameters, the value of which changes during the pre-pulse phase. Also disclosed herein are graphical user interfaces (GUIs) that allow the selection of waveforms configured to selectively modulate or activate specific neural targets or selected ratios of the neural targets. Adjustable parameters of the waveforms are adjusted automatically based on selection of user-defined parameters.

14 Claims, 16 Drawing Sheets

(58) Field of Classification Search
CPC .. A61N 1/36146; A61N 1/025; A61N 1/0551; A61N 1/36062
See application file for complete search history.

(56) References Cited

U.S. PATENT DOCUMENTS

| | | | |
|---|---|---|---|
| 7,024,247 | B2 | 4/2006 | Gliner et al. |
| 7,424,322 | B2 | 9/2008 | Lombardi et al. |
| 7,450,992 | B1 | 11/2008 | Cameron |
| 8,255,057 | B2 | 8/2012 | Fang et al. |
| 8,335,664 | B2 | 12/2012 | Eberle |
| 8,606,362 | B2 | 12/2013 | He et al. |
| 8,620,436 | B2 | 12/2013 | Parramon et al. |
| 8,768,453 | B2 | 7/2014 | Parramon et al. |
| 9,044,155 | B2 | 6/2015 | Strahl |
| 9,061,140 | B2 | 6/2015 | Shi et al. |
| 9,119,964 | B2 | 9/2015 | Marnfeldt |
| 9,248,274 | B2 | 2/2016 | Troosters et al. |
| 9,248,279 | B2 | 2/2016 | Chen et al. |
| 9,302,112 | B2 | 4/2016 | Bornzin et al. |
| 9,403,013 | B2 | 8/2016 | Walker et al. |
| 9,409,020 | B2 | 8/2016 | Parker |
| 9,526,897 | B2 | 12/2016 | Chen et al. |
| 9,731,116 | B2 | 8/2017 | Chen |
| 10,076,667 | B2 | 9/2018 | Kaula et al. |
| 2008/0139497 | A1 | 6/2008 | Yang |
| 2008/0294211 | A1* | 11/2008 | Moffitt ............... A61N 1/36167 607/9 |
| 2011/0009923 | A1 | 1/2011 | Lee |
| 2012/0095529 | A1 | 4/2012 | Parramon et al. |
| 2015/0051665 | A1* | 2/2015 | Hershey ............. A61N 1/36071 607/46 |
| 2015/0360038 | A1 | 12/2015 | Zottola et al. |
| 2016/0184591 | A1 | 6/2016 | Feldman et al. |
| 2016/0213927 | A1* | 7/2016 | McGee ................ A61N 1/0551 |
| 2017/0259065 | A1 | 9/2017 | Baru et al. |
| 2018/0071513 | A1 | 3/2018 | Weiss et al. |
| 2018/0071520 | A1 | 3/2018 | Weerakoon et al. |
| 2018/0264278 | A1 | 9/2018 | Laghi |

OTHER PUBLICATIONS

Hennings, Kristian, et al., "Orderly Activation of Human Motor Neurons Using Electrical Ramp Prepulses," Clinical Neurophysiology, 116, 2005, pp. 597-604.

Grill, WM and Mortimer, JT. "Stimulus waveforms for selective neural stimulation." IEEE EMBS. vol. 14(4) 1995.

Kirsch AD, et al., "Anodic Versus Cathodic Neurostimulation of the Subthalamic Nucleus: A Randomized-Controlled Study of Acute Clinical Effects," Parkinsonism and Related Disorders, 55, 2018, pp. 61-67.

McIntyre CC, Grill WM., "Selective Microstimulation of Central Nervous System Neurons," Ann Biomed Eng., Mar. 2000, 28(3):219-33.

McIntyre CC, Grill WM., "Excitation of Central Nervous System Neurons by Nonuniform Electric Fields," Biophys Journal, vol. 76(2), Feb. 1999, pp. 878-888.

Merrill, Daniel R., et al., "Electrical Stimulation of Excitable Tissue: Design of Efficacious and Safe Protocols," Journal of Neuroscience Methods, 141, 2005, pp. 171-198.

Part No. MSP430 data sheet, manufactured by Texas Instruments, retrieved from <http://www.ti.com/lsds/ti/microcontroller/16-bit_msp430/overview.page?DCMP=MCU_other&HQS=msp430>.

Vercise PC Deep Brain Stimulation System: Vercise Navigator 1.0 Programming Guide, Boston Scientific, NM-320907-AA, Jan. 2016, 16 pages.

Wolter, Tilman, "Spinal Cord Stimulation for Neuropathic Pain: Current Perspectives," Journal of Pain Research, Nov. 18, 2014, 7, pp. 651-663.

* cited by examiner

| Waveform Parameters ||
|---|---|
| Defined (Constrained) | Adjustable |
| Biphasic Pulse, Ratio of Amplitude of Primary and Secondary Pulse, Amplitude of Primary Pulse, Charge Balance | Pulse Width of Secondary Pulse |
| Triphasic Pulse (pre-pulse, primary, secondary), amplitude ratio of each pulse, charge balance, pulse width of two of the pulses. | Pulse width of Unconstrained Pulse |
| Triphasic Pulse (pre-pulse, primary, secondary), pulse width of each pulse, charge balance, amplitude of two of the pulses. | Amplitude of Unconstrained Pulse |
| Biphasic Pulse, Ratio of Amplitudes of both Pulses, Amplitude of Both Pulses | Ratio of Active/Passive Charge Recovery |

*Figure 18*

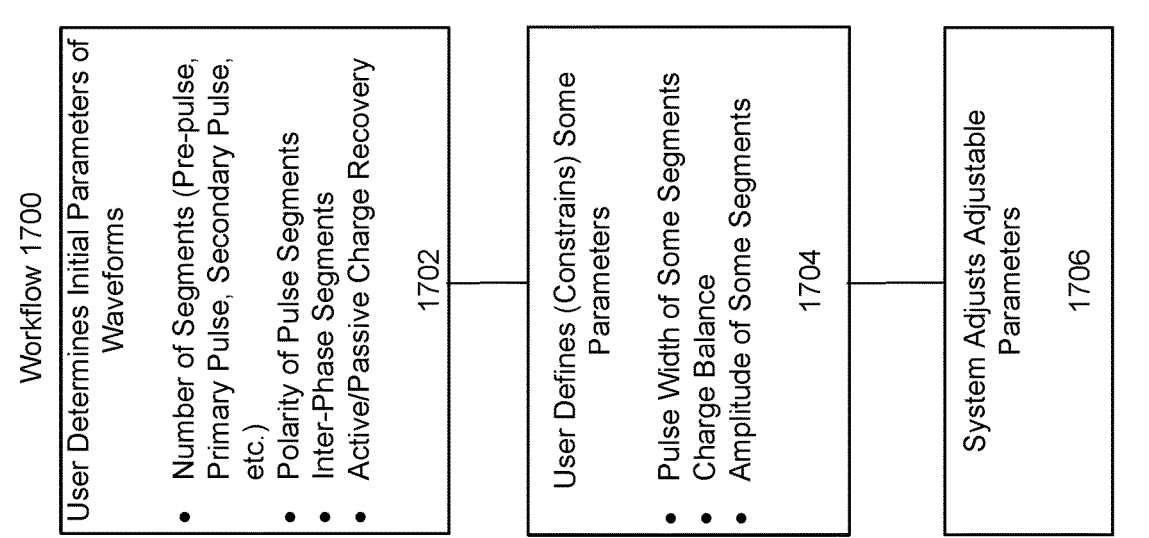

*Figure 17*

NEUROSTIMULATION SYSTEM FOR DELIVERING SELECTIVITY MODES

CROSS REFERENCE TO RELATED APPLICATIONS

This is a non-provisional application of U.S. Provisional Patent Application Ser. No. 62/663,563, filed Apr. 27, 2018, to which priority is claimed, and which is incorporated herein by reference in its entirety.

FIELD OF THE INVENTION

The present invention relates generally to medical device systems, and more particularly to pulse generator systems for neural stimulation.

INTRODUCTION

Implantable stimulation devices are devices that generate and deliver stimuli to nerves and nervous tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, and other neural stimulators to treat urinary incontinence, sleep apnea, shoulder subluxation, etc. The description that follows will generally focus on the use of the invention within a Deep Brain Stimulation (DBS) system, such as is disclosed in U.S. Patent Application Publication 2016/0184591. However, the present invention may find applicability in any implantable stimulator system, such as Spinal Cord Stimulation (SCS) systems as disclosed in U.S. Pat. No. 6,516,227 as well as other neuromodulation modalities, such as vagus nerve stimulation (VNS), hypoglossal nerve stimulation, peripheral nerve stimulation, and the like.

As shown in FIG. 1, a DBS system typically includes an Implantable Pulse Generator (IPG) 10, which includes a biocompatible device case 12 formed of titanium for example. The case 12 typically holds the circuitry and battery 14 necessary for the IPG to function, although IPGs can also be powered via external energy and without a battery. The IPG 10 is coupled to electrodes 16 via one or more electrode leads (two such leads 18 and 20 are shown), such that the electrodes 16 form an electrode array 22. The electrodes 16 are carried on a flexible body 24, which may also house individual signal wires 26 coupled to each electrode. In the illustrated embodiment, there are eight electrodes on lead 18, labeled E1-E8, and eight electrodes on lead 20, labeled E9-E16, although the number of leads and electrodes is application specific and therefore can vary. The proximal ends of leads 18 and 20 couple to the IPG 10 using lead connectors 28, which are fixed in a header material 30 comprising an epoxy for example.

In a DBS application, as is useful in the treatment of Parkinson's disease for example, the IPG 10 is typically implanted under the patient's clavicle (collarbone), and the leads 18 and 20 are tunneled through the neck and between the skull and the scalp where the electrodes 16 are implanted through holes drilled in the skull in the left and right and side of the patient's brain, as shown in FIG. 2. In one example, the electrodes 16 may be implanted in the subthalamic nucleus (STN). The electrodes may be implanted in both of these regions in the left and right side of the brain, meaning that four leads might be necessary, as discussed in the above-referenced '591 Publication. Stimulation therapy provided by the IPG 10 has shown promise in reducing a patient's Parkinson's symptoms, in particular, tremors that can occur in the patient's extremities.

FIG. 3 shows an environment in which an implant patient can be "fitted," that is, where stimulation parameters for a patient can experimented with to hopefully find parameters that alleviate a patient's symptoms (e.g., tremor) while not introducing unwanted side effects. Stimulation is typically provided by pulses, and stimulation parameters typically include the amplitude of the pulses (whether current or voltage), the frequency and duration of the pulses, as well as the electrodes 16 selected to provide such stimulation, and whether such selected electrodes are to act as anodes (that source current to the tissue) or cathodes (that sink current from the tissue).

In FIG. 3, one or more of leads 18, 20 have been implanted in the patient's tissue 35 at a target location 36 such as the STN as described above. The proximal ends of lead(s) 18, 20 can either be connected to an IPG 10 also implanted in the tissue 35, which IPG 10 includes stimulation circuitry 31 programmed to provide stimulation to the electrodes 16 consistent with the prescribed stimulation parameters. The proximal ends of lead(s) 18, 20 can also be at least temporarily connected to an External Trial Stimulation 72, which is typically used to provide stimulation during a trial phase after the lead(s) 18, 20 are implanted but before the IPG 10 is permanently implanted. The proximal ends of lead(s) 18, 20 exit an incision 71 in the patient's tissue 35, and are connected to the ETS 72. The ETS 72 mimics operation of the IPG 10 to provide stimulation pulses to the tissue, and so also includes programmable stimulation circuitry 31. The ETS 72 allows a clinician to experiment with the stimulation parameters, and allows the patient to try stimulation for a trial period before the IPG 10 is permanently implanted.

Regardless whether trial stimulation is occurring via the ETS 72 or permanent stimulation is occurring via the IPG 10, a clinician programmer (CP) system 50 is shown that can be used by a clinician to adjust the stimulation parameters. The CP system 50 includes a computing device 51, such as a desktop, laptop, or notebook computer, a tablet, a mobile smart phone, a Personal Data Assistant (PDA)-type mobile computing device, etc. (hereinafter "CP computer"). In FIG. 3, CP computer 51 comprises a laptop computer that includes typical computer user interface means such as a screen 52, a mouse, a keyboard, speakers, a stylus, a printer, etc., not all of which are shown for convenience. Also shown in FIG. 3 are accessory devices for the CP system 50 that are usually specific to its operation as a stimulation controller, such as a communication wand 54, and a joystick 58, which can be connected to suitable ports on the CP computer 51, such as USB ports 59 for example. Joystick 58 is generally used as an input device to select various stimulation parameters (and thus may be redundant of other input devices to the CP), but is also particularly useful in steering currents between electrodes to arrive at an optimal stimulation program.

In operation, the clinician will use the user interface of the CP computer 51 to adjust the various stimulation parameters the ETS 72 or IPG 10 will provide, and such adjusted parameters can be wirelessly transmitted to the patient. Such wireless transmission can occur in different ways. The antenna used in the CP system 50 to communicate with the ETS 72 or IPG 10 can depend on the data telemetry antenna included in those devices. If the patient's ETS 72 or IPG 10 includes a coil antenna 70a or 40a, the wand 54 can likewise include a coil antenna 56a to establish communication over a near-field magnetic induction link at small distances. In this instance, the wand 54 may be affixed in close proximity to the patient, such as by placing the wand 54 in a holster, belt, or necklace wearable by the patient and proximate to the patient's ETS 72 or IPG 10.

If the ETS 72 or IPG 10 includes a far-field RF antenna 70b or 40b with longer communication distance, the wand 54, the CP computer 51, or both, can likewise include a short-range RF antenna 56b to establish communication with the ETS 72 or IPG 10. (In this example, a CP wand 54 may not be necessary if the CP computer 51 has the necessary short-range RF antenna 56b). If the CP system 50 includes a short-range RF antenna 56b, such antenna can also be used to establish communication between the CP system 50 and other devices, and ultimately to larger communication networks such as the Internet. The CP system 50 can typically also communicate with such other networks via a wired link 62 provided at a Ethernet or network port 60 on the CP computer 51, or with other devices or networks using other wired connections (e.g., at USB ports 59). Far-field RF antennas 56b, 70b, and/or 40b may operation with well-known communication standards such as Bluetooth, WiFi, ZigBee, MICS, etc.

To program stimulation parameters, the clinician interfaces with a clinician programmer graphical user interface (CP GUI) 64 provided on the display 52 of the CP computer 51. As one skilled in the art understands, the CP GUI 64 can be rendered by execution of CP software 66 on the CP computer 51, which software may be stored in the CP computer's non-volatile memory 68. One skilled in the art will additionally recognize that execution of the CP software 66 in the CP computer 51 can be facilitated by control circuitry 70 such as a microprocessor, microcomputer, an FPGA, other digital logic structures, etc., which is capable of executing programs in a computing device. Such control circuitry 70 when executing the CP software 66 will in addition to rendering the CP GUI 64 enable communications with the ETS 72 or IPG 10 as explained earlier, so that the clinician can use the CP GUI 64 to program the stimulation parameters to the stimulation circuitry 31 in the patient's ETS 72 or IPG 10. Examples of the CP GUI 64 can be found in U.S. Patent Application Publication 2015/0360038 and U.S. Provisional Patent Application Ser. No. 62/471,540, filed Mar. 15, 2017.

A hand-held, portable patient external controller 50 can also be used to adjust stimulation parameters, which may include one or both of a coil antenna 52a or an RF antenna 52b capable of communicating with the ETS 72 of IPG 10. Further details concerning an external controller 50 can be found in the above-referenced '038 Publication.

SUMMARY

Aspects of the disclosure describe a neuromodulation system, comprising: a first device comprising a non-transitory computer-readable medium comprising instructions configured to cause a microcontroller to: cause one or more electrodes to provide a stimulation waveform at the one or more electrodes, wherein the stimulation waveform comprises: at least one stimulation phase, and one or more of at least one pre-pulse phase or one post-pulse phase, wherein the at least one pre-pulse phase or at least one post-pulse phase is defined by at least one parameter, and wherein the value of the at least one parameter changes during the at least one pre-pulse phase or at least one post-pulse phase, and wherein at least a part of the at least one pre-pulse phase or the at least one post-pulse phase is opposite polarity than the at least one stimulation phase. According to some embodiments, the at least one parameter comprises amplitude. According to some embodiments, the value of the at least one parameter increases during the at least one pre-pulse phase or at least one post-pulse phase. According to some embodiments, the value of the at least one parameter decreases during the at least one pre-pulse phase or at least one post-pulse phase. According to some embodiments, the value of the at least one parameter ramps between a first value and a second value during the at least one pre-pulse phase or at least one post-pulse phase. According to some embodiments, the ramp is analog. According to some embodiments, the ramp is digital. According to some embodiments, the value of the at least one parameter steps between a first value and a second value during the at least one pre-pulse phase or at least one post-pulse phase. According to some embodiments, the at least one parameter is amplitude, and the value of the amplitude changes from a value below a threshold to a value above the threshold during the at least one pre-pulse phase or at least one post-pulse phase. According to some embodiments, the threshold is an initial recruitment threshold for a non-target neural element. According to some embodiments, the non-target neural element is selected from neuronal cells and fibers of passage. According to some embodiments, the first device is an implantable pulse generator (IPG). According to some embodiments, the non-transitory computer-readable medium is control circuitry of the IPG. According to some embodiments, the first device is a clinician programmer. According to some embodiments, the first device is an external controller.

Further aspects of the disclosure provide a method of preferentially stimulating target neural elements, the method comprising: applying a stimulation waveform to a tissue comprising the target neural elements and non-target neural elements, wherein the stimulation waveform comprises: at least one stimulation phase, and one or more of at least one pre-pulse phase or one post-pulse phase, wherein the at least one pre-pulse phase or at least one post-pulse phase is defined by at least one parameter, and wherein the value of the at least one parameter changes during the at least one pre-pulse phase or at least one post-pulse phase, and wherein at least a part of the at least one pre-pulse phase or the at least one post-pulse phase is opposite polarity than the at least one stimulation phase. According to some embodiments, the at least one parameter comprises amplitude. According to some embodiments, the value of the at least one parameter increases during the at least one pre-pulse phase or at least one post-pulse phase. According to some embodiments, the value of the at least one parameter decreases during the at least one pre-pulse phase or at least one post-pulse phase. According to some embodiments, the value of the at least one parameter ramps between a first value and a second value during the at least one pre-pulse phase or at least one post-pulse phase. According to some embodiments, the ramp is analog. According to some embodiments, the ramp is digital. According to some embodiments, the value of the at least one parameter steps between a first value and a second value during the at least one pre-pulse phase or at least one post-pulse phase. According to some embodiments, the at least one parameter is amplitude, and the value of the amplitude changes from a value below a threshold to a value above the threshold. According to some embodiments, the threshold is an initial recruitment threshold for a non-target neural element.

According to some embodiments, the non-target neural element is selected from neuronal cells and fibers of passage.

Further aspects of the disclosure provide a non-transitory computer-readable medium comprising instructions configured to cause a microcontroller to: cause one or more electrodes implanted in a patient to issue a stimulation waveform at the one or more electrodes, wherein the stimulation waveform comprises: at least one stimulation phase, and one or more of at least one pre-pulse phase or one post-pulse phase, wherein the at least one pre-pulse phase or at least one post-pulse phase is defined by at least one parameter, and wherein the value of the at least one parameter changes during the at least one pre-pulse phase or at least one post-pulse phase, and wherein at least a part of the at least one pre-pulse phase or the at least one post-pulse phase is opposite polarity than the at least one stimulation phase. According to some embodiments, the at least one parameter comprises amplitude. According to some embodiments, the value of the at least one parameter increases during the pre-pulse phase. According to some embodiments, the value of the at least one parameter decreases during the pre-pulse phase during the at least one pre-pulse phase or at least one post-pulse phase. According to some embodiments, the value of the at least one parameter ramps between a first value and a second value during the at least one pre-pulse phase or at least one post-pulse phase. According to some embodiments, the ramp is analog. According to some embodiments, the ramp is digital. According to some embodiments, the value of the at least one parameter steps between a first value and a second value during the at least one pre-pulse phase or at least one post-pulse phase. According to some embodiments, the at least one parameter is amplitude, and the value of the amplitude changes from a value below a threshold to a value above the threshold. According to some embodiments, the threshold is an initial recruitment threshold for a non-target neural element. According to some embodiments, the non-target neural element is selected from neuronal cells and fibers of passage.

Also disclosed herein is a non-transitory computer readable medium comprising instructions executable on an external device comprising a graphical user interface (GUI) for programming an implantable pulse generator (IPG), wherein the instructions comprise an algorithm, wherein the algorithm, when executed is configured to: provide a plurality of candidate waveforms, wherein each waveform is configured to selectively modulate a different ratio of two neural targets, receive, via the GUI of the external device, one or more inputs indicating a selected ratio of the two neural targets, and in response to the one or more inputs, select a stimulation waveform configured to modulate the selected ratio from among the candidate waveforms. According to some embodiments, the candidate waveforms are formed based on one or more templates defining one or more parameters for one or more phases of each of the candidate waveforms based on the selected ratio of neural targets. According to some embodiments, the one or more phases of the candidate waveforms are selected from the group consisting of pre-pulse phases, primary phases, secondary phases, and inter-phase segments. According to some embodiments, the one or more parameters are selected from the group consisting of amplitude, duration, attack envelope, rise time, digital resolution, beginning/ending amplitude ratio, number of pulses, and time between pulses. According to some embodiments, the two neural targets are different neural elements. According to some embodiments, the two neural targets are cells and fibers of passage. According to some embodiments, the two neural targets are different potential activity sites within the same type of neural element. According to some embodiments, the two neural targets are selected from the group consisting of cells bodies, axons, axon bend/curves, axon hillocks, dendritic trees, and synapses. According to some embodiments, the two neural targets differ from each other based on geometry, orientation, or environment. According to some embodiments, the GUI comprises a slider bar configured to select the selected ratio of the two neural targets.

Also disclosed herein is an external device comprising a graphical user interface (GUI) for programming an implantable pulse generator (IPG), wherein the device comprises a non-transitory computer-readable medium comprising instructions configured to: receive, via the GUI, one or more inputs specifying one or more user defined stimulation waveform parameters, based on the one or more inputs, automatically adjust one or more system adjustable stimulation waveform parameters, and generate a stimulation waveform based on the user defined stimulation parameters and system adjustable stimulation parameters, and provide the stimulation waveform to the IPG. According to some embodiments, the GUI displays a graphical representation of the stimulation waveform. According to some embodiments, the graphical representation reflects the one or more user defined stimulation waveform parameters and the automatically adjusted one or more system adjustable stimulation waveform parameters. According to some embodiments, the GUI comprises one or more slider bars for defining the one or more user defined stimulation waveform parameters.

BRIEF DESCRIPTION OF THE DRAWINGS

FIG. 17 shows a workflow for adjusting waveform parameters.

FIG. 18 shows defined and adjustable waveform parameters.

DESCRIPTION

Figures 1, 2:
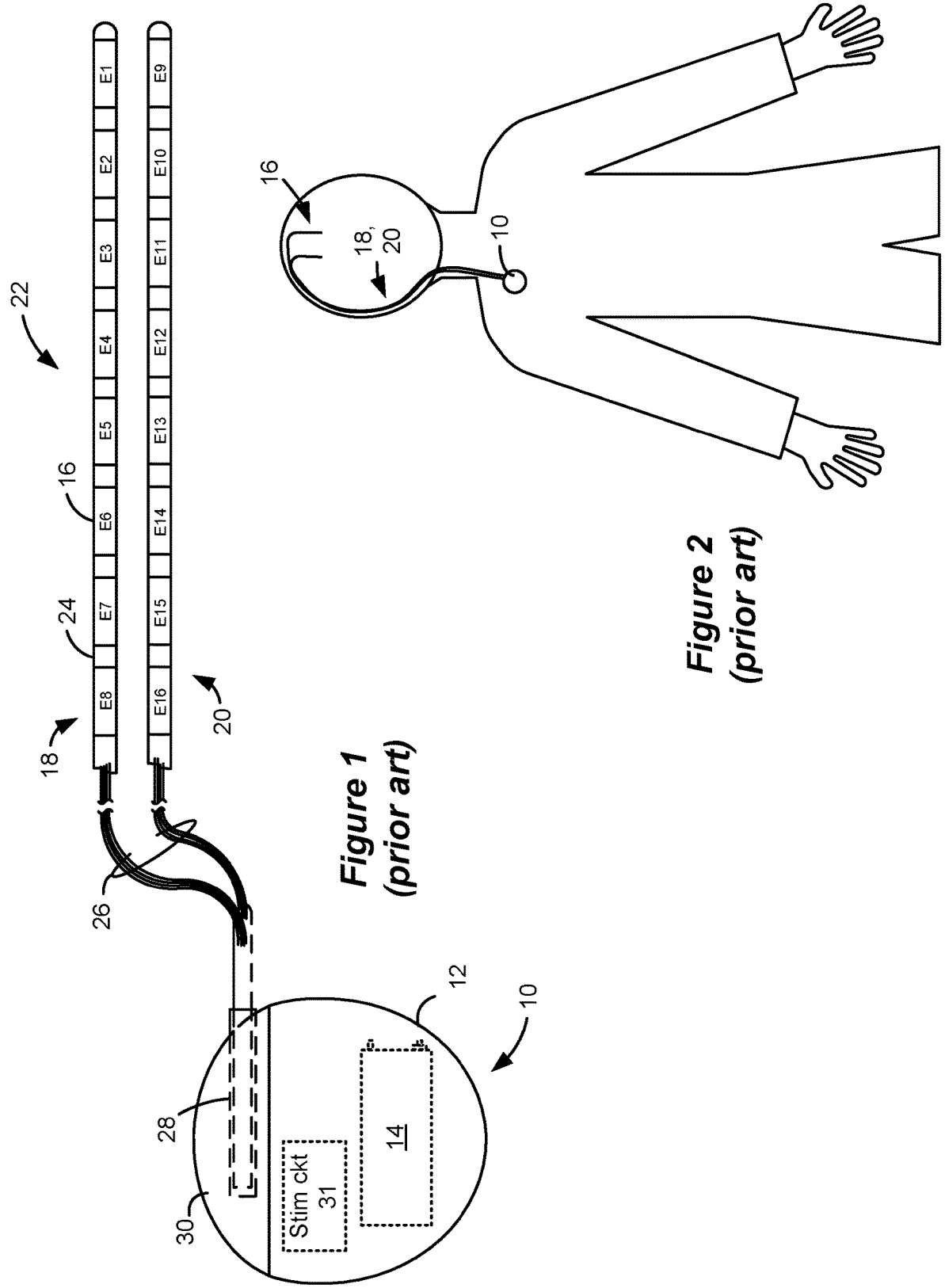
FIG. 1 shows an implantable pulse generator (IPG) system for neuromodulation.
FIG. 2 shows IPG implanted in a patient.
Figure 3:
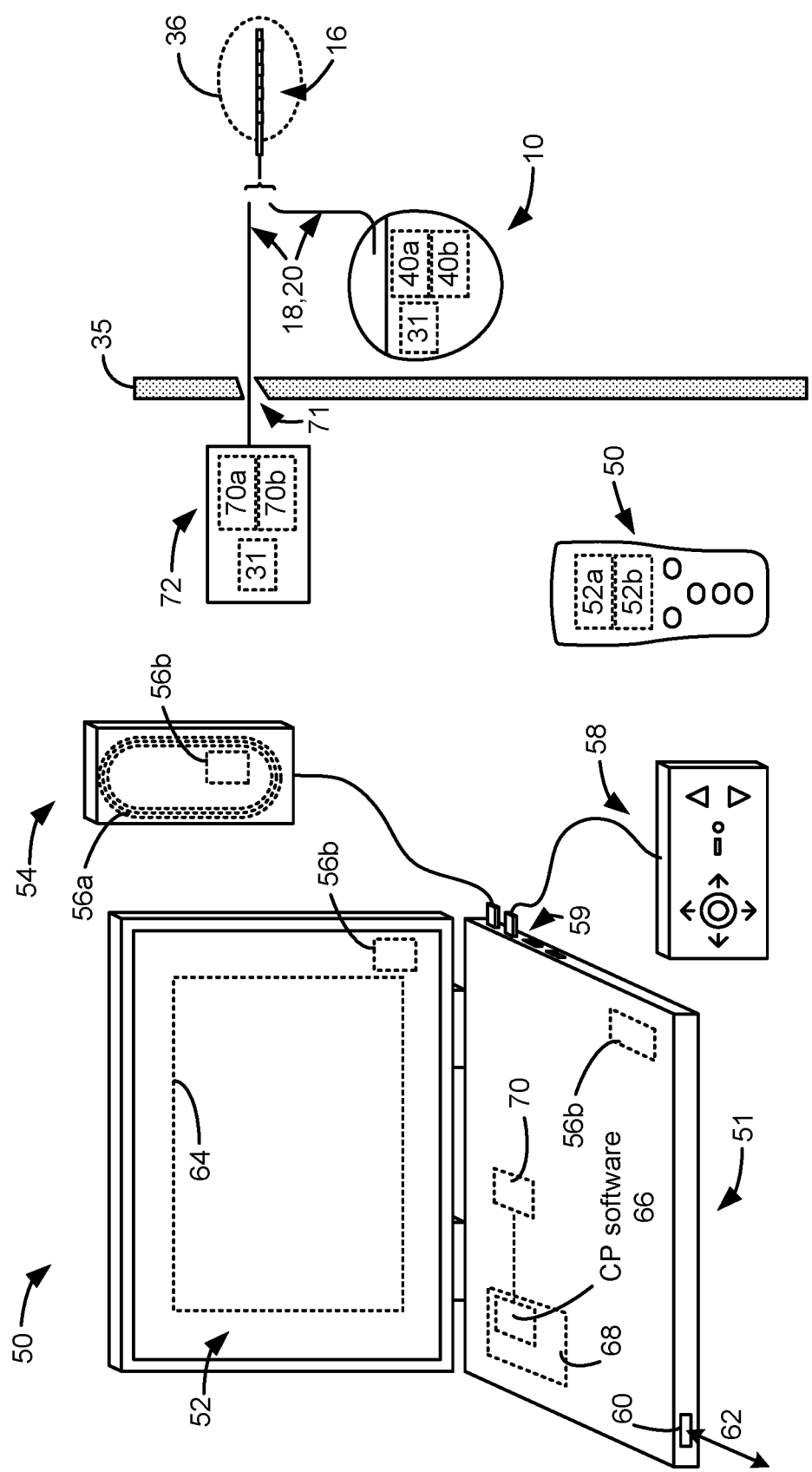
FIG. 3 shows a system for programming an IPG.
Figure 4A:
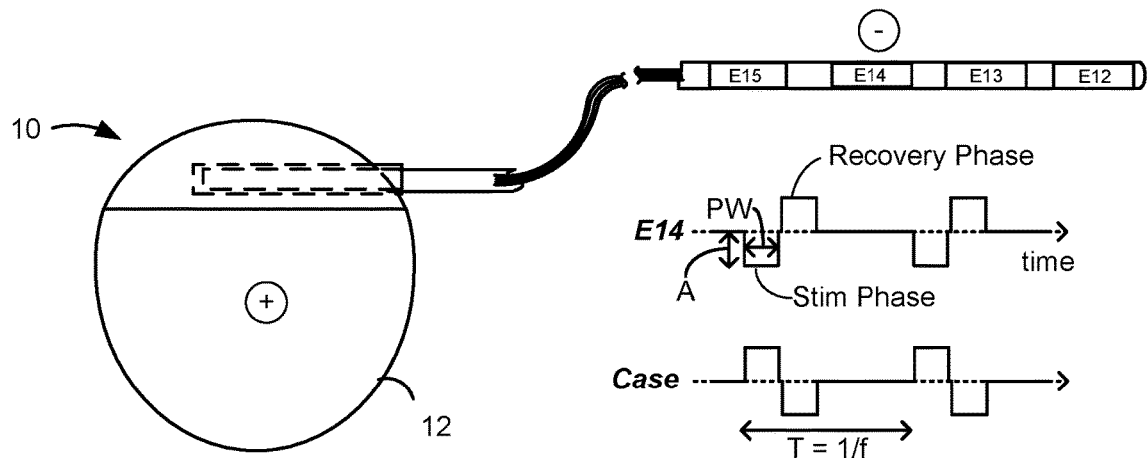
FIGS. 4A-4C show waveforms generated using an IPG.
Figure 4B:
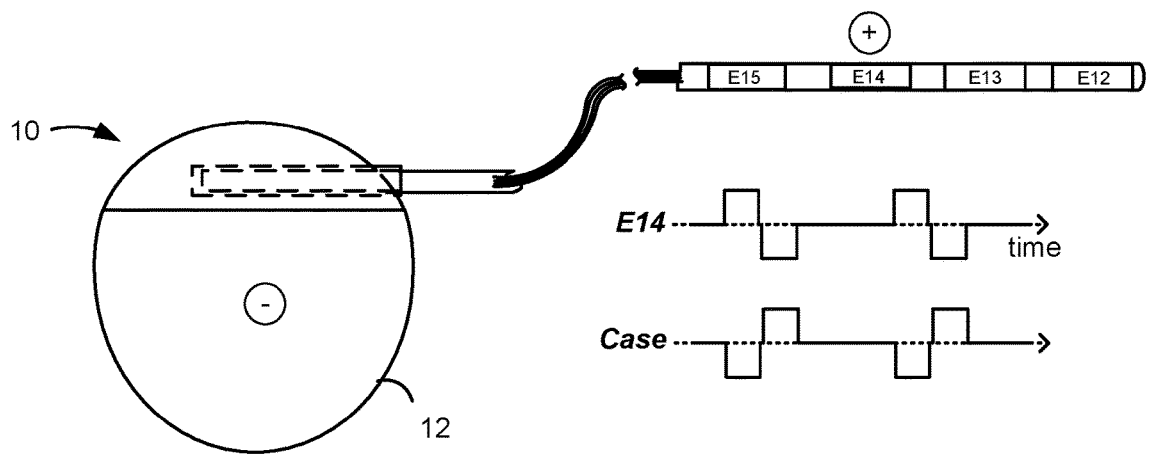
Figure 4C:
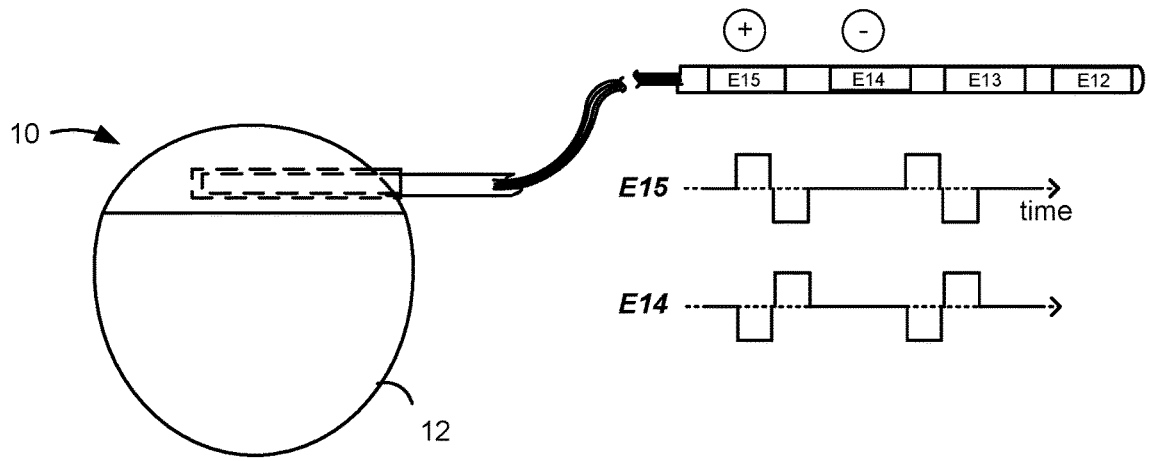

FIGS. 4A-4C illustrate examples of stimulation waveforms executable by the IPG 10. In FIG. 4A, electrode E14 is selected as the cathode and the case 12 of the IPG functions as an anode. In FIG. 4B, electrode E14 is selected as the anode and the case functions as the cathode. In FIG. 4C, electrode E14 functions as the cathode and electrode E15 functions as the anode. The pulse width (PW) of the stimulation phase, the frequency (f) and the amplitude (A) of the pulses is also shown. Although not shown, more than two electrodes (including the case 12) can be active at any given time. For example, electrode E14 could comprise an anode providing a +10 mA current pulse amplitude, while electrodes E13 and E15 could both comprise cathodes with −7 mA and −3 mA current pulse amplitudes, respectively. Another example might be using a lead electrode (e.g., E14) as an anode and having both the case 12 and another lead electrode (e.g., E15) share cathode duty.

In the example shown, each stimulation pulse is biphasic, meaning it comprises a first pulse phase (denoted in the drawings as a stimulation phase) followed thereafter by an opposite polarity pulse phase (denoted in the drawings as a recovery phase). The pulses as shown comprise pulses of constant current, and notice that the amplitude of the current at any point in time is equal but opposite such that current injected into the patient's tissue by one electrode (e.g., E14) is removed from the tissue by the other electrode (e.g., case 12). Notice also that the area of the stimulation and recovery pulse phases are equal, ensuring active charge recovery of the same amount of charge during each pulse phase. Although not shown, monophasic pulses—having only a first pulse phase (i.e., a stimulation phase) but not followed by an active-charge recovery second pulse phase—can also be used. In such cases, passive charge recovery can be used. In some cases, there may be an unbalanced first and second pulse, followed by a balancing passive charge recovery phase. In other cases, the net charge delivered by a pulse as described herein remains imbalanced, either indeterminately, or until a later time in which further balancing is achieved.

The effects of neurostimulation depend on many factors, including the amplitude, frequency and waveform characteristics of the stimulation pulses. For example, the polarity of the stimulation pulse can affect the types of neural elements that are recruited during the stimulation. It is known that monophasic cathodic pulses selectively recruit axon fibers (a.k.a. axons of passage) compared to local nerve cells. Conversely, monophasic anodic pulses selectively recruit nerve cells compared to fibers. See U.S. Pat. No. 6,560,490. When biphasic pulses are used, a cathodic stimulation phase followed by an anodic recovery phase selectively recruits fibers, but the selectivity may be greatly diminished compared to the use of monophasic cathodic pulse. Likewise, an anodic stimulation phase followed by a cathodic recovery phase is selective for cell recruitment, but again, that selectivity may be diminished compared to a monophasic anodic pulse.

Figure 5:
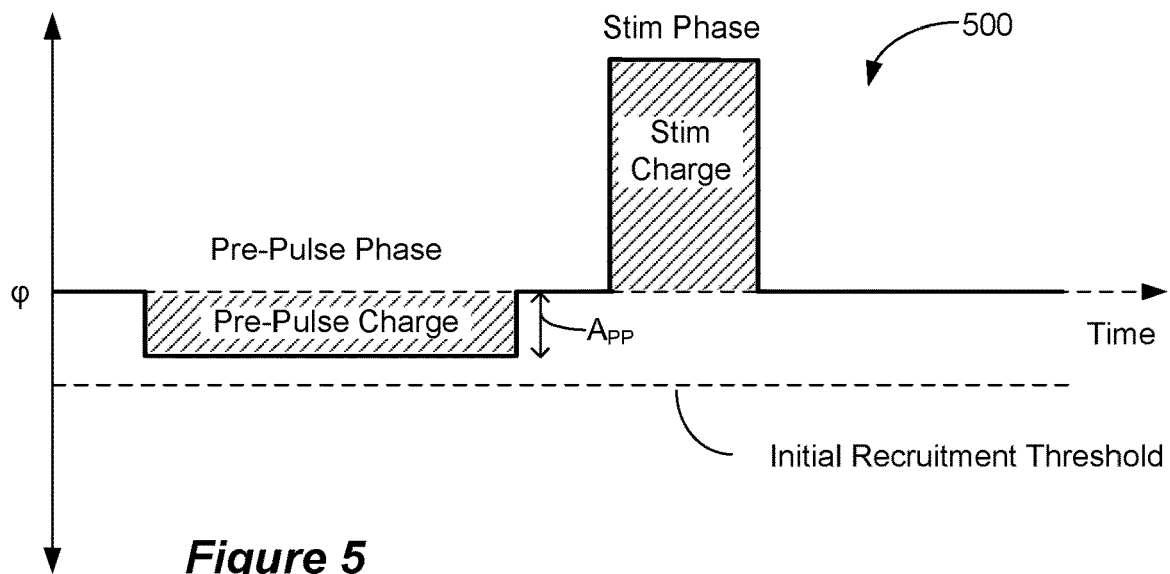
FIG. 5 shows a waveform having an anodic stimulation phase with a cathodic pre-pulse phase.

U.S. Pat. No. 6,560,490 describes asymmetric charge-balanced stimulation waveforms that can selectively recruit either fibers or cells. FIG. 5 illustrates a waveform 500 purported to selectively recruit nerve cells (the targeted neural element) compared to fibers (non-targeted neural element). The waveform 500 includes a cathodic pre-pulse phase and an anodic stimulation phase. Note that the two phases are charge-balanced, i.e., the charge passed during the low amplitude pre-pulsing phase is about equal to the charge passed during the anodic stimulation phase. Note also that the amplitude of the pre-pulse phase $A_{PP}$, remains below a recruitment threshold (referred to herein as an "initial recruitment threshold" for reasons explained below) and, therefore, does not recruit appreciable number of non-targeted neural elements. As the stimulation phase is anodic, it is expected to preferentially recruit cells compared to fibers.

It is important to note that the pre-pulse phase of waveform 500 is amplitude-limited. In other words, if the amplitude of the pre-pulse phase $A_{PP}$ exceeds the initial recruitment threshold, the pre-pulse phase will begin to recruit non-targeted neural elements (mostly fibers, as the pre-pulse phase is cathodic), and the selectivity of the overall waveform 500 will suffer as a result.

The amplitude-limited nature of the waveform 500 imposes limitations on its usefulness. For example, since the amount of current that can be applied during pre-pulsing is limited, the strength and depth of the electric field is likewise limited, which in turn limits the population of neural elements that can be impacted with the waveform 500.

As the pre-pulse progresses in time, the non-target neural elements become less excitable, and therefore the amplitude of the pre-pulse phase can increase without stimulating the non-target neural elements. In other words, the recruitment threshold increases with time. That is why the recruitment threshold at the beginning of stimulation is referred to herein as the "initial threshold."

Figure 6:
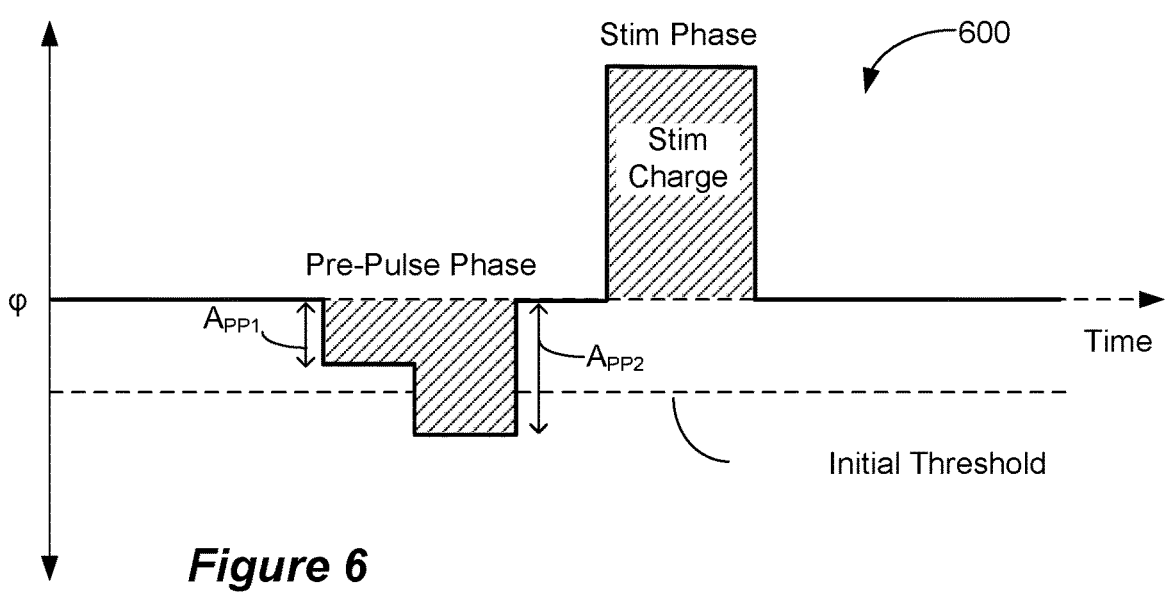
FIG. 6 shows a waveform having an anodic stimulation phase and a complex cathodic stimulation pre-pulse.

FIG. 6 illustrates a waveform 600 that capitalizes on this discovery. The waveform 600 includes a complex pre-pulsing phase that comprises a first pre-pulse amplitude $A_{PP1}$ that is below the initial recruitment threshold. Since the non-target neural elements become less excitable as pre-pulsing progresses, the amplitude of the pre-pulsing phase can be increased to an amplitude $A_{PP2}$ that exceeds the initial recruitment threshold without recruiting non-target neural elements. Thus, the spatial influence of the waveform 600 can be extended.

Figure 7:
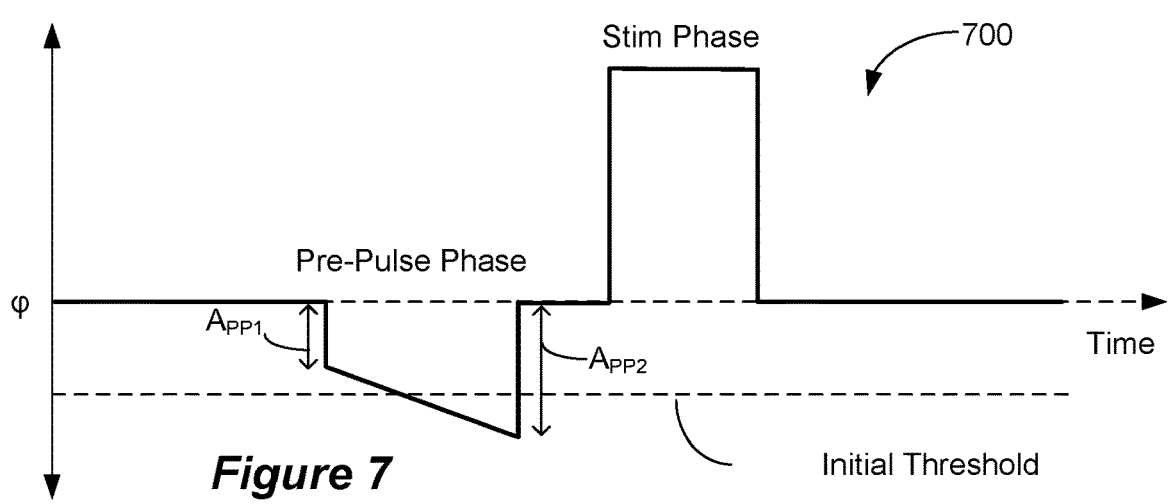
FIG. 7 shows a waveform having an anodic stimulation phase and a ramped cathodic pre-pulse phase.
Figure 8:
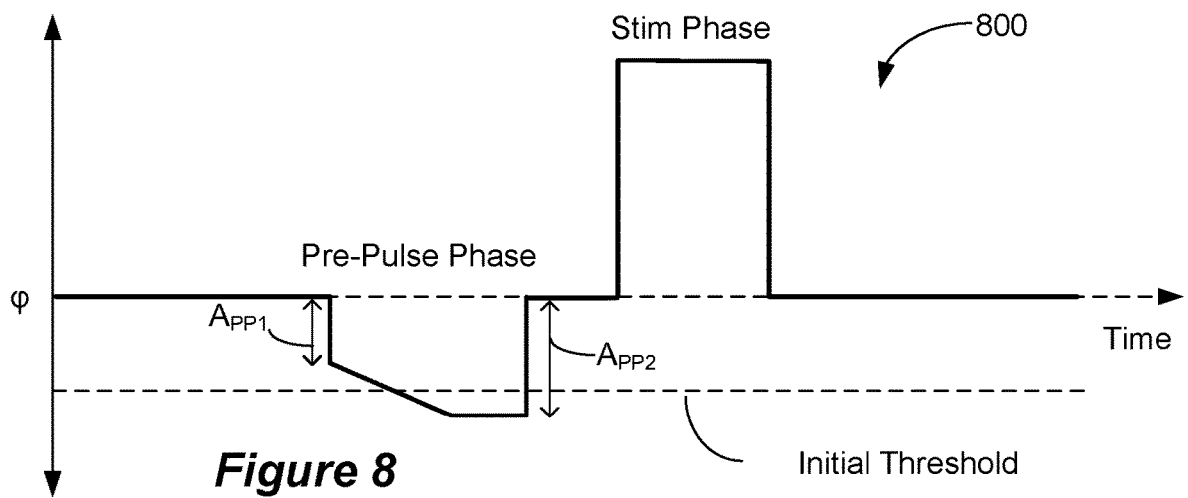
FIG. 8 shows a waveform having an anodic stimulation phase and a cathodic pre-pulse phase with a ramp and a plateau.

The amplitude of the pre-pulse phase need not be increased in a stepwise fashion as illustrated in FIG. 6. FIGS. 7 and 8 illustrate alternative waveforms 700 and 800, respectively. Waveform 700 features a monotonically increasing cathodic pre-pulse phase having an amplitude that begins below the initial recruitment threshold, but that exceeds the initial recruitment threshold as pre-pulsing progresses. Waveform 800 (FIG. 8) features an increasing cathodic pre-pulse phase, followed by a plateau.

Figure 9:
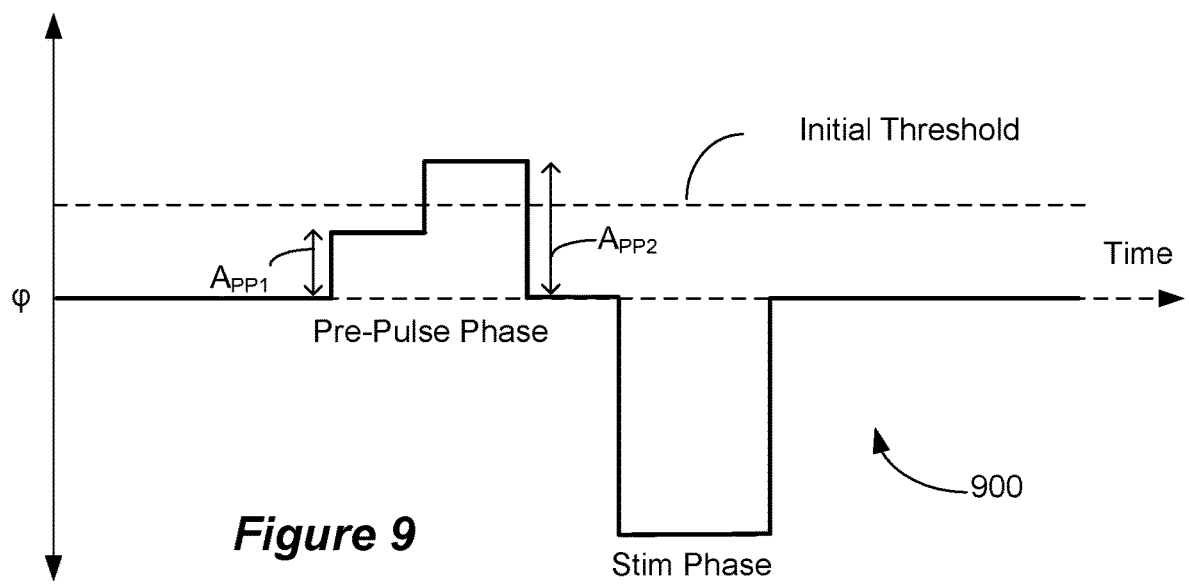
FIG. 9 shows a waveform having a cathodic stimulation phase and a complex anodic pre-pulse phase.

The waveforms 600, 700, and 800 feature cathodic pre-pulse phases and anodic stimulation phases, and therefore preferentially target stimulation of nerve cells compared to fibers of passage. FIG. 9 illustrates a waveform 900 having a complex anodic pre-pulse phase and a cathodic stimulation phase, which preferentially targets fibers compared to cells. As with the cathodic pre-pulse phases illustrated in waveforms 600, 700, and 800, the anodic pre-pulse phases may include other complex shapes or functions, such as ramps and/or plateaus with amplitudes that begin below the initial recruitment threshold and exceed the initial recruitment threshold as pre-pulsing progresses.

The complex waveforms described above demonstrate how waveforms can be tailored to selectively target either fibers or cells. Stated more generally, the waveform can be tailored to selectively effect a first target (Target A) compared to a second target (Target B). In the examples above, the Target A is cells and Target B is fibers of passage. However, the waveforms can be tailored to selectively (or discriminatively) target other aspects of a patient's neurology. For example, the waveform can be tailored to selectively effect large fibers (Target A) versus small fibers (Target B). The waveforms can be tailored to distinguish between classes or groups of neural elements, whereby some classes or groups comprise of different portions of the same whole, e.g. modulating the site of maximum action along a single type of neural element. As an example, Target A may be bends or curves along axons of a neural element and Target B may be axon hillocks within the same neural element. Such modes of targeting and discrimination are discussed in more detail below.

Aspects of the disclosure provide methods and algorithms whereby waveforms can be tailored to provide such targeting/discrimination by automatically tailoring or adjusting various phases or segments of the waveform. FIG. 10A illustrates a generic waveform 1020. The illustrated waveform 1020 is divided into multiple segments or phases. The illustrated waveform comprises two pre-pulsing phases (segments) PP1, and PP2, a stimulation phase S1, two post-pulse phases S2 and S3, and two inter-phase segments IP1 and IP2. It should be noted that these phases are examples and other phases/segments may be defined.

FIGS. 6 through 9 illustrate how the pre-pulsing phase(s) can be tailored to provide selectivity between two neural targets, such as cells versus fibers. It should be noted here that the inter-phase segments IP1 and/or IP2 and post-pulse phases (such as S2 and/or S3) can also be tailored to provide target specificity. For example, referring to FIG. 10 A, assume that the pre-pulse phases PP1 and PP2 are configured to preferentially desensitize Target A (for example fibers) and the stimulation phase S1 is configured to preferentially modulate Target B (for example, cells). Further Target B modulation specificity is affected by increasing the second inter-phase segment IP2 and decreasing the amplitude of the post-pulse phases S2 and/or S3 (and increasing the duration of S2 and/or S3 to affect charge recovery).

According to embodiments disclosed herein, various attributes of the segments/phases of the waveforms are adjusted to provide a desired targeting/discrimination. For example, polarity, amplitude, duration and/or other metadata, e.g., rise time, ramp, ring, digital resolution of an analog envelope, etc. can be defined and adjusted. For example, instead of adjusting the stimulation current in a stepwise manner (i.e., defining an amplitude and duration for each of the phases), an amplitude ramp or other function may be defined, as discussed above regarding FIGS. 7 and 8. Likewise, instead of defining phases in terms of segments and duration, frequencies and/or percent charge recovery for each attribute can be defined. As explained in more detail below, the waveform is defined and adjusted based on one or more templates relating to the mode of selectivity chosen by the user.

Aspects of this disclosure provide algorithms and methods for providing waveforms tailored to selectively stimulate (or activating) a desired ratio of different neural populations. FIG. 10B illustrates a series of waveforms, 1002, 1004, 1006, 1008, 1010, and 1012. As seen, each of the waveforms are realized by adjustments to the phases/segments (PP1, PP2, IP1, S1 and S2) of the generic waveform 1020. The waveforms provide a range of specificity of Target A versus Target B. Again, in the illustrated example, Target A may correspond to cells and Target B may correspond to fibers of passage. But as explained above, other targets may be chosen.

In the illustrated example, waveform 1002 is most specific for Target A and waveform 1012 is most specific for Target B. The waveform that is most selective for A is referred to herein as the "Limit" with respect to A; likewise, the waveform that is most selective for B is referred to as the "Limit" with respect to B. The continuum of selectivity between the two limits is referred to herein as a "selectivity dimension." The algorithms described herein provide a continuum of candidate waveforms, ranging from a waveform that is most selective for activating population A to a waveform that is most selective for activating population B.

FIG. 10C illustrates a notional representation 1000 of percent activation (or modulation) of Target A as a function of percent activation (or modulation) of Target B using the waveforms 1002, 1004, 1006, 1008, 1010, and 1012. For example, curve 1002 of FIG. 10C notionally corresponds to waveform 1002 of FIG. 10B. In the representation 1000 amplitude is increased to moving along the curves from left to right. The specific amplitude required for a particular target may vary with the distance of the target from the electrode(s) and the intervening tissue. Further, the different targets may be at difference distances from the stimulation.

Referring to curve 1002 in representation 1000, which is the selectivity curve notionally related the waveform 1002 of FIG. 10B, it is seen that as stimulation intensity (amplitude) increase moving from left to right along curve 1002, both Target A and Target B are modulated, but Target A is modulated to a greater degree. For example, at point 1014 on the curve about 80% of Target A is activated and only about 40% of Target B is modulated. The waveforms 1004, 1006, and 1008 become less and less selective for Target A and waveforms 1010 and 1012 become more selective for Target B.

The diagonal line 1016 represents a continuum (i.e., the selectivity dimension) corresponding to candidate waveforms between waveforms 1002 (the "Limit" with respect to Target A) and 1012 (the "Limit" with respect to Target B). An appropriate stimulation waveform can be selected from among the candidate waveforms within the selectivity dimension to activate (or modulate) a desired ratio of the targets. Note that the ratio is determined by both the selected 'selectivity curve' and the amplitude. In other words, the ratio of targets may change based on the amplitude of stimulation. Upon selection of a desired Target A/Target B activation ratio, the system described herein adjusts the stimulation waveform to provide a waveform for the desired ratio of modulation. As described in more detail below, the user is presented with a user interface (i.e., a GUI), whereby the user can select where along the selectivity dimension they wish to stimulate. For example, the GUI may include a slider allowing the user to select where along the continuum they wish to stimulate. Upon selection, the system adjusts waveform to provide the appropriate candidate waveform to provide the desired stimulation. In some embodiments, the user may make incremental changes to the setting of the selectivity dimension, and corresponding incremental changes to the waveform are made. This approach allows the user to make changes in the selectivity dimension at a non-zero amplitude (i.e., without having to reduce the amplitude to zero to evaluate a next selectivity setting).

Figure 10:
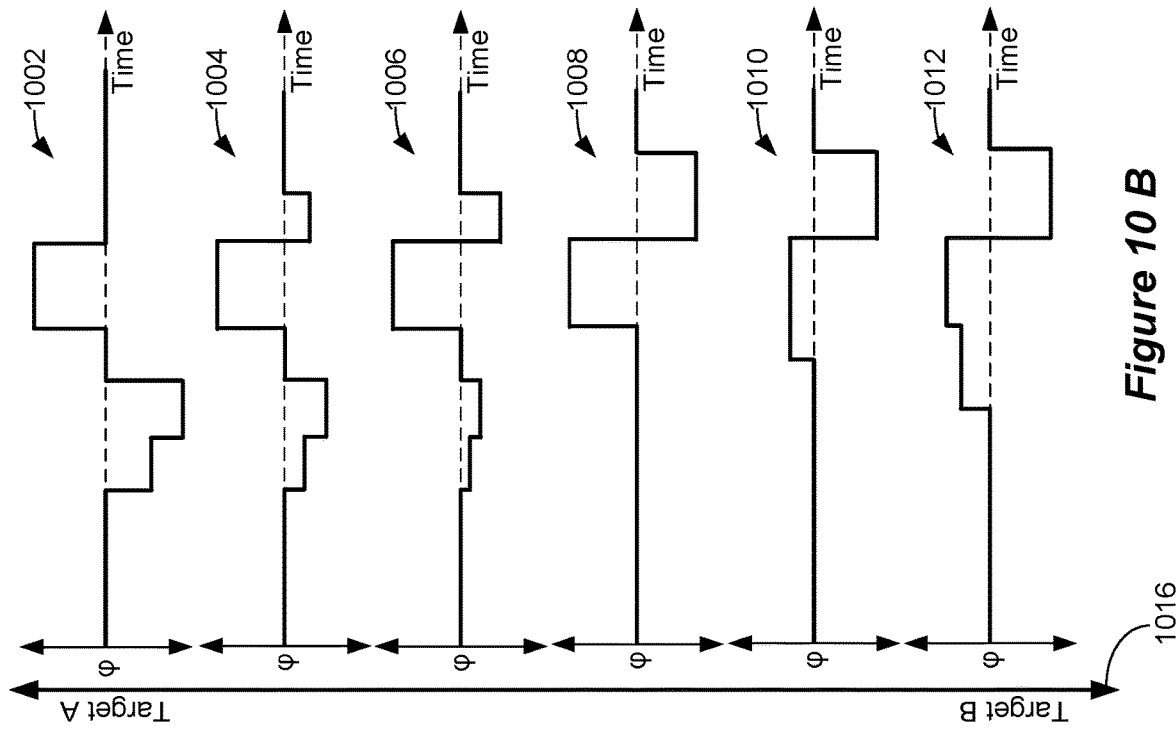
FIG. 10A shows a representative waveform.
FIG. 10B shows a series of waveforms
FIG. 10C shows selectivity curves and a selectivity dimension.
Figure 10:
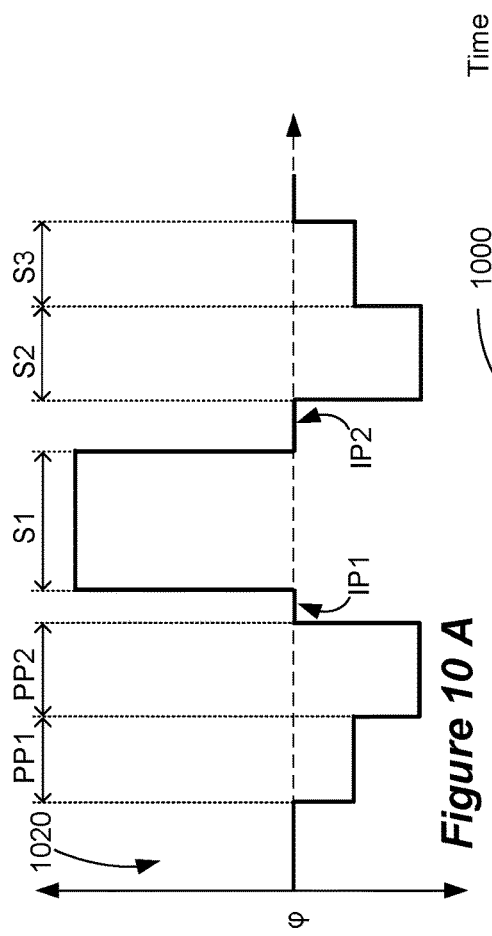
Figure 10:
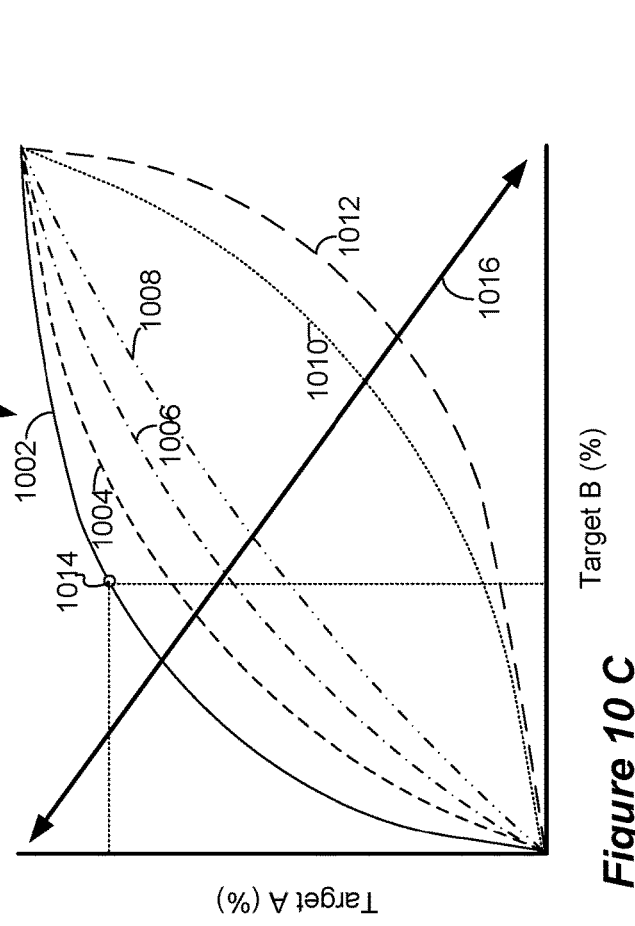
Figure 11:
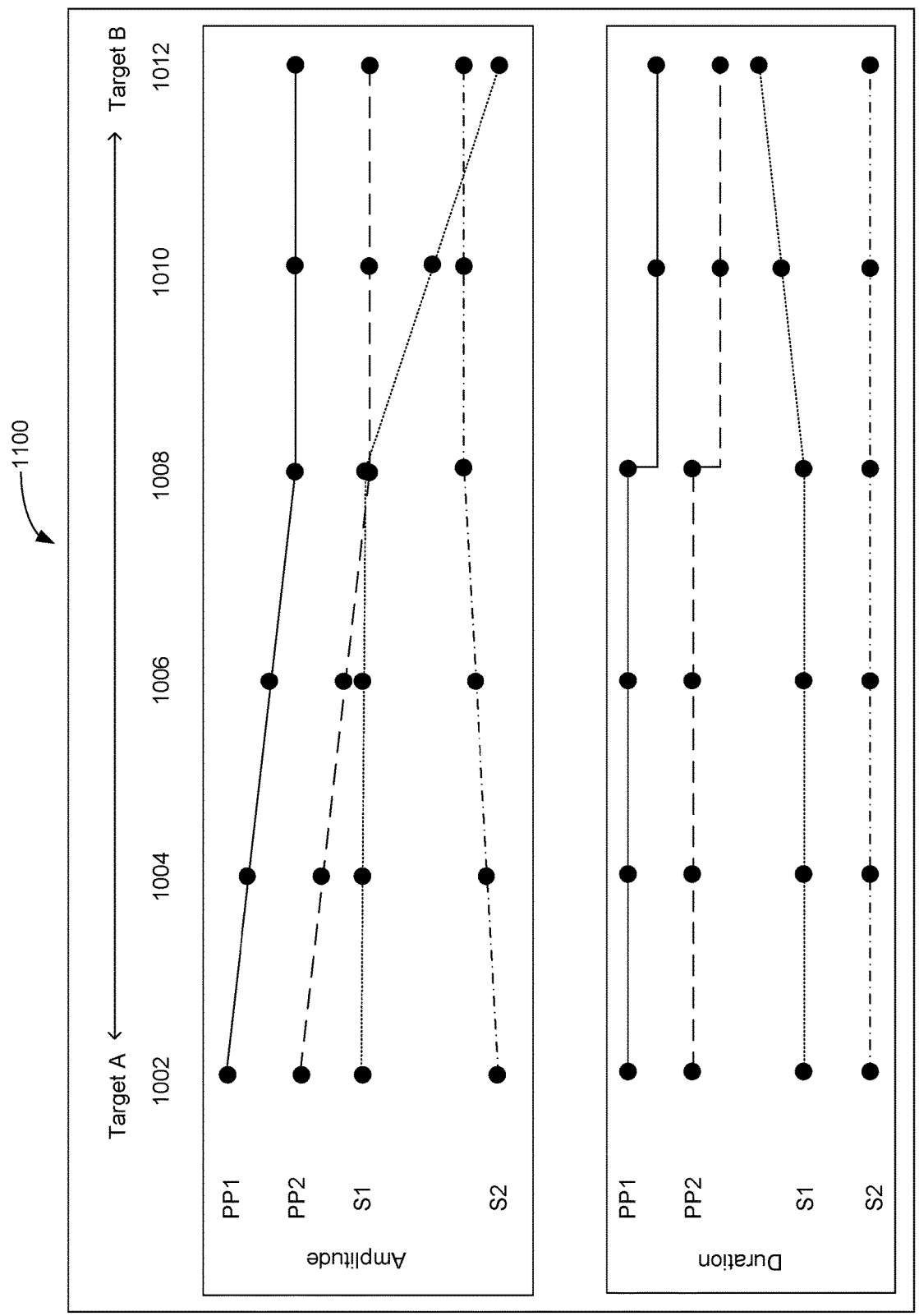
FIG. 11 shows a template for providing waveforms with selectivity.

FIG. 11 shows a notional template 1100 defining how the amplitude and duration of the waveform phases/segments PP1, PP2, S1, and S2 (described above) are adjusted to transition between candidate waveforms 1002 to 1012 (FIGS. 10 B and 10 C). For example, as described by the template 1100, the amplitudes of the cathodic pre-pulse segments PP1 and PP2 decrease along the transition between selectivity for Target A to selectivity for Target B. Past waveform 1008, the segments PP1 and PP2 are not active. Likewise, the amplitude of the anodic stimulation pulse S1 remains constant until the transition between Target A/Target B selectivity is reached (waveform 1008). At that point, the amplitude of S1 swings cathodic and its duration increases. Past the transition, S1 behaves as an anodic pre-pulse desensitizing the non-targeted cells and sensitizing the targeted cells. It should be noted that in template 1100 discrete values for each of the phases PP1, PP2, etc., are shown for the corresponding waveforms 1002, 1004, etc. However, as mentioned above, some embodiments allow the user to make incremental changes to the setting of the selectivity dimension thereby affecting corresponding incremental changes to the waveform. In other words, incremental changes to the setting of the selectivity dimension results in values for the phases PP1, PP2, etc. that are between those illustrated for 1002, 1004, etc. For example, the values may be on the lines connecting the dots in template 1100.

As noted above, additional aspects of the waveform may be defined and controlled by the template. For example, the template may include additional metadata and or transfer functions that are active during some or all the positions along the selectivity dimension. For example, the template may include additional waveform phases that are only active during a portion of the template. Attack envelopes, rise times, digital resolutions, beginning/ending amplitudes and the like may be defined at various positions for various waveforms within the template. For example, the template may include one or more metadata aspects, such as "attack," which may be always set to a category, such as "instant," or to a transfer function, such as a ramp or rise time set to zero for all phases (as plotted) or may set to different values at different instances within the template. As another example, one or more phases of the waveform may be set to "square wave," but could also be set to provide sawtooth, triangle, pseudo-sine, pseudo-gaussian, waves, etc. The template may define how any of the parameters change along the selectivity dimension.

Figure 12:
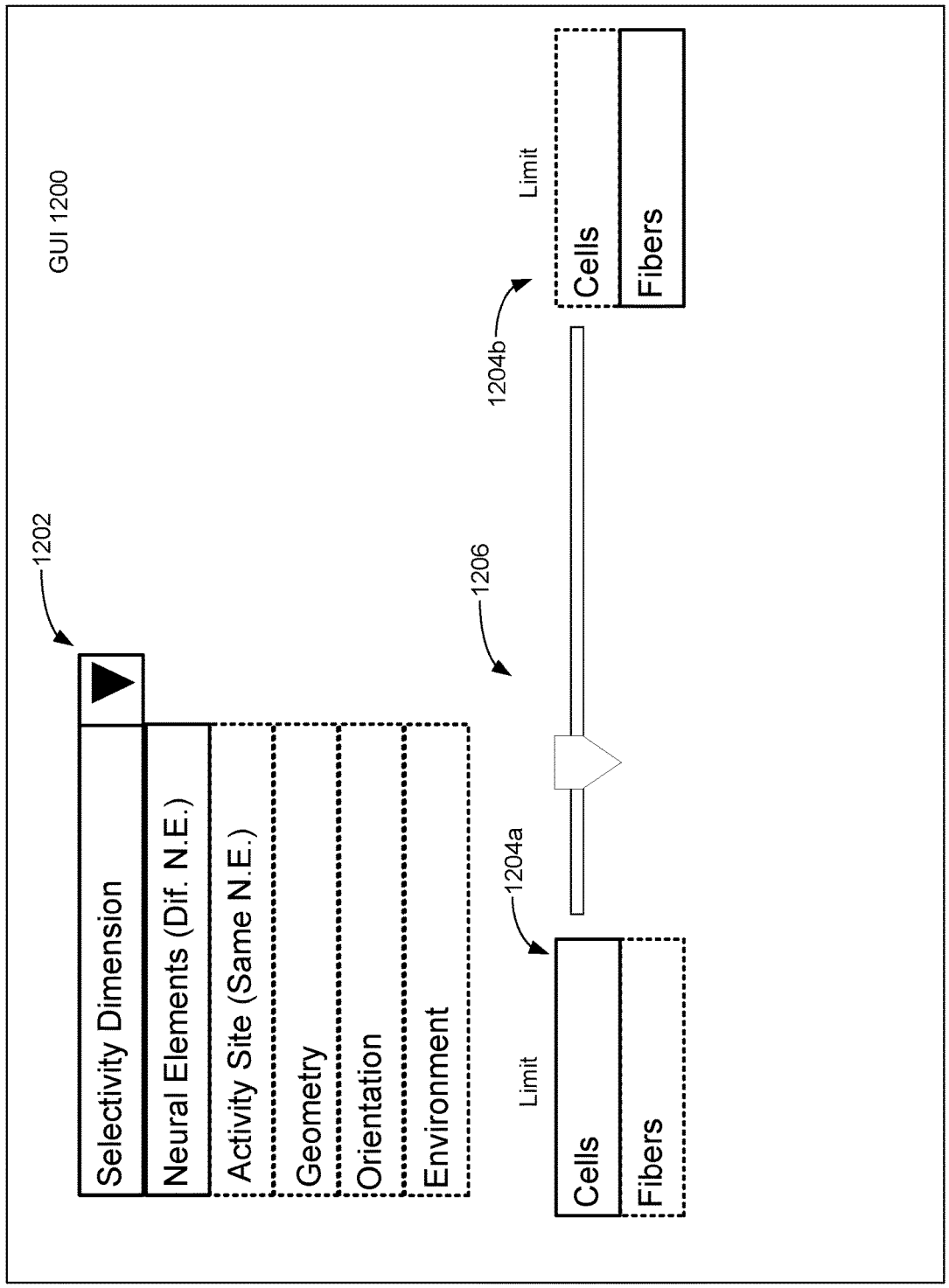
FIG. 12 shows a graphical user interface (GUI) for selecting a waveform.

FIG. 12 illustrates an instantiation of a GUI portion 1200 for selecting stimulation parameters along a selectivity dimension (continuum). The GUI portion 1200 includes a dropdown menu 1202 for choosing from among available selectivity dimensions. In other words, the dropdown menu allows a user to select the categories of selectivity, from which the user can select Target A and Target B. In the GUI portion 1200 illustrated in FIG. 12, the Neural Elements Selectivity Dimension, allowing a user to select stimulation along a fiber/cell selectivity dimension, as described above. Other potential selectivity dimensions may be available, as discussed in more detail below.

Upon choosing a Selectivity Dimension, appropriate limits for the particular selectivity dimension are presented for selection in windows 1204a and 1204b. In FIG. 12, Cells is selected as one limit (1204a) and Fibers is selected as the other limit (1204b). When the selectivity dimension and limits are selected using the GUI portion 1200, the system loads the appropriate template(s) defining the candidate waveforms having stimulation parameters relevant to the selection.

The GUI portion 1200 further includes a slider bar 1206, whereby the user can select where along the chosen selectivity dimension (and limits) to stimulate. In FIG. 12, when the slider is positioned further to the left, a waveform from among the candidate waveforms having parameters that preferentially stimulate cells is applied (based on the loaded template, e.g., template 1100 of FIG. 11). When the slider is positioned to the right, a waveform from among the candidate stimulation waveform having parameters that preferentially stimulate fibers of passage is applied (based on the loaded template). The slider bar 1206 can be thought of as a graphical representation of the diagonal line 1016 of FIG. 10. As the ratio of targeted elements may change as a function of the stimulation amplitude, as mentioned above, the slider bar may also be thought of as a graphical representation of a family of diagonal lines 1016, each corresponding to a different stimulation amplitude.

Figure 13:
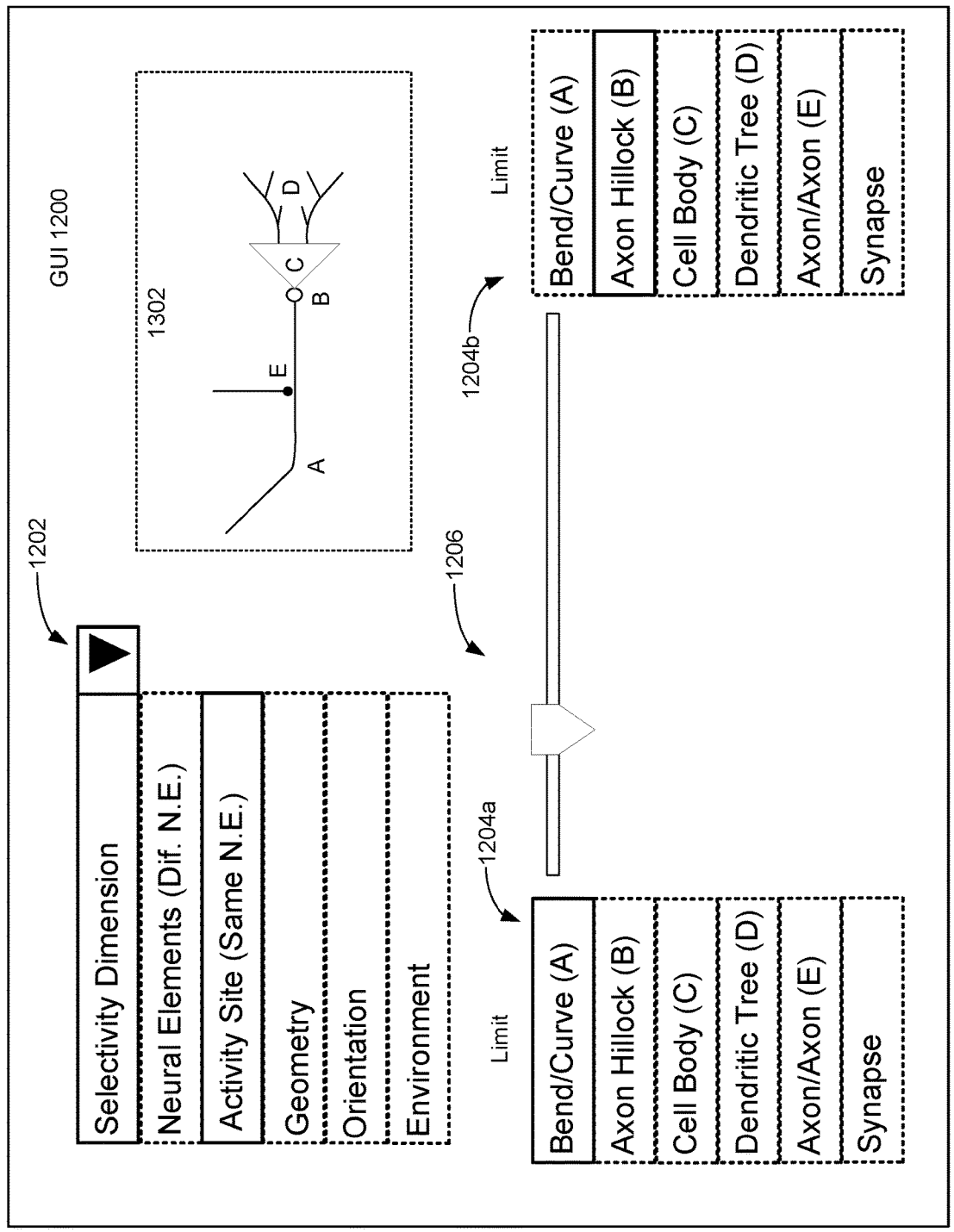
FIG. 13 shows graphical user interface (GUI) for selecting a waveform.

To this point, the discussion has focused on recruitment of different neural elements, e.g., fibers of passage versus cells, as a selectivity dimension and the discussion has focused on templates for affecting the selection along the fiber/cell selectivity dimension. However, the methods and systems described herein allow additional selectivity dimensions. For example, FIG. 13 illustrates a further instantiation of a GUI portion 1200, wherein Activity Site (within the same neural element(s)) is selected in the menu 1202 as the Selectivity Dimension. Choosing Activity Site as the Selectivity Dimension populates windows 1204a and 1204b with the parts of neural elements that can be targeted as the primary site of action for neural stimulation. According to some embodiments, a graphical representation 1302 of such activity sites may be presented. In the instantiation of the GUI portion 1200 illustrated in FIG. 13, Bend/Curve is selected as one limit (1204a) and Axon Hillock is selected as the other limit (1204b). Thus, the GUI instantiation illustrated in FIG. 13 allows a user to select from among candidate waveforms that primarily affect Bend/Curve activity and candidate waveforms that primarily affect Axon Hillock activity. The slider bar 1206 is used to select waveforms that stimulate a desired ratio of those two activity sites. Upon these selections in the GUI, the system loads and executes the appropriate templates to provide the requisite waveforms to provide the desired stimulation.

It should be noted here, that in FIG. 13, only a single slider bar 1206 and only two limits are presented. However, multiple slider bars may be presented, allowing multiple Limits to be defined. Alternatively, a multi-dimensional selection area (such as a square) may be provided, allowing more than two limits to be defined.

Additional selectivity dimensions are provided, including but not limited to neural element geometry, neural element orientation, neural element biophysics (e.g., gating parameters, time constants), and neural element environment (complex conductivity/permittivity). It should be noted that the selectivity dimension may be defined and selected based on therapeutic factors instead of (or in addition to) the neural factors described above. For example, the selectivity dimension may be between two (or more) therapeutic outcomes. An ideal presentation might present the user lists of side effects and benefits, based on anatomy, and allow the user to specify selectivity of the various side effects and benefits. For example, a patient may have rigidity, and to stimulate the appropriate target, some non-target regions are going to have to be stimulated, for example, facial pulling and tremor.

The clinician is able to preferentially select stimulation of the facial pulling region over the tremor region because the particular patient is not as susceptible to facial pulling as they are to tremor. As the complexity of the detailed waveform GUI would be hidden from the user by the templates, the complexity of the templates and neural element selection in FIGS. 12 and 13 would be hidden by the GUI that allows the user to prioritize side effects and benefits. In such a case, the template accounts for the structure and function of the neural anatomy, electrode placement, and mapping of stimulation parameters to particular therapeutic outcomes.

Figure 14:
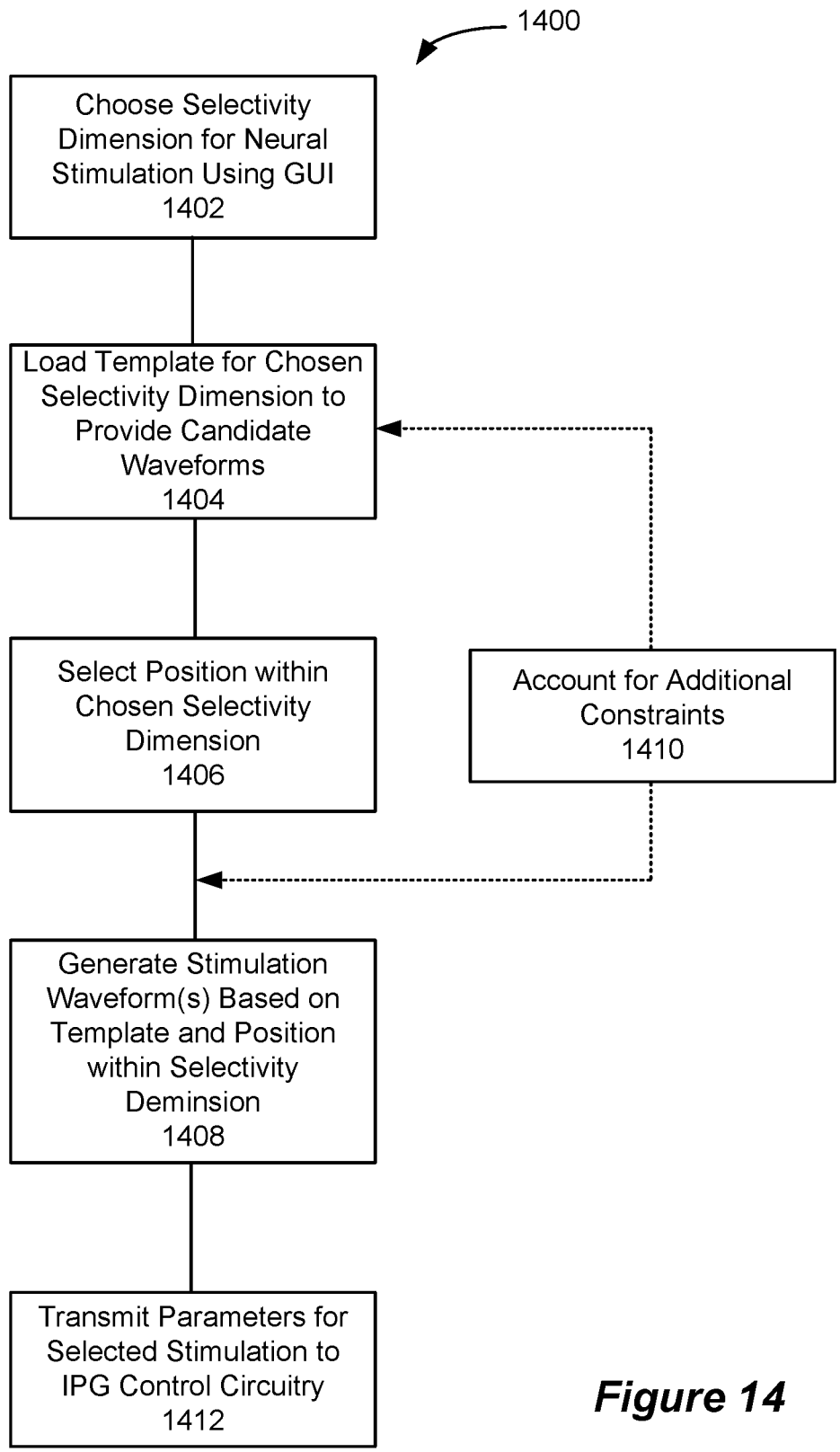
FIG. 14 shows a workflow for providing stimulation waveforms within a selectivity dimension.

FIG. 14 illustrates an example of a general workflow based on the systems and methods described above. A user (typically a clinician) chooses a selectivity dimension for neural stimulation using the GUI 1402. As described above, the user may choose to preferentially stimulate cells v. fibers, or to stimulate a selected site of action of neural elements, etc. It should be noted that, according to some embodiments, only one selectivity dimension may be provided by the system (e.g., cells vs fibers) such that the step of choosing the dimension is not required (because it is the only dimension available).

The system then loads the appropriate template for the chosen selectivity dimension 1404. For example, if the Neural Elements Selectivity Dimension is selected (i.e., cells v. fibers), the system may load a template such as template 1100 (FIG. 11). The templates may be crafted by hand or generated automatically. For example, the templates may be derived and/or optimized based on models. According to some embodiments, the templates may be based on look-up tables correlating stimulation parameters to stimulation outcomes. The templates may be stored in a library. The templates provide candidate waveforms from which a waveform can be selected.

The user then chooses where along the chosen selectivity dimension they wish to stimulate 1406. For example, if the selectivity dimension is based on different neural elements, the user may wish to selectively activate 40% fibers and 60% cells. The system then provides the appropriate stimulation waveform(s) from among the candidate waveforms using the selectivity dimension template based on the user's chosen position within the selectivity dimension 1408.

It should be noted that additional constraints in addition to the position within the chosen selectivity dimension may be implicated in deriving the appropriate waveforms. For example, the user may wish to stimulate at least 60% of a targeted neural element and 40% of the non-targeted neural element. But the proposed therapy might be constrained by factors relating to safety, energy cost, etc. Or, in addition to the relative stimulation of target/non-target neural elements, the user may be concerned about other therapeutic variables, such as temperature, pH, glial calcium flux, increased blood flow, CSF flow, blood cell count, enzymatic activity, mitochondrial activity, or reactive oxygen species release, as examples. Thus, the workflow 1400 may include steps for accounting for such additional constraints 1410. According to some embodiments, constraints are built into the templates themselves. Additionally (or alternatively) the waveforms built according to the templates may be further modified to account for such constraints. Some constraints may be designed to limit waveforms from a perspective of stimulation acceptability, compatibility, tolerability, or safety.

Once the waveforms have been provided in the system based on the chosen selectivity dimension, position within the selectivity dimension, and any additional constraints, instructions for executing the waveforms are transmitted to control circuitry of the IPG 1412. The IPG can generate the waveforms, as described below.

Also disclosed herein are methods and a user interface for designing and controlling waveforms. FIGS. 15A, 15B, 16A, and 16B illustrate examples of a waveform 1500, 1502, 1600, and 1602, respectively.

Figure 15:
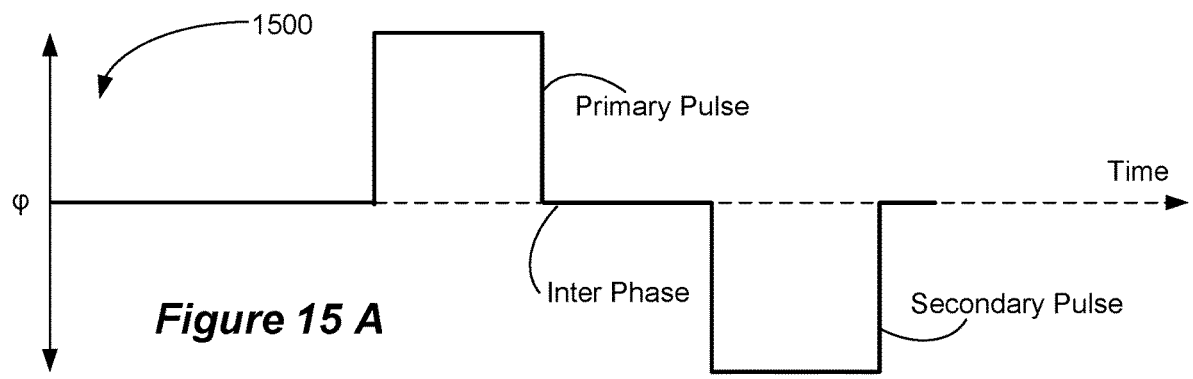
FIGS. 15A and 15B show adjustment of waveform phases.
Figure 15:
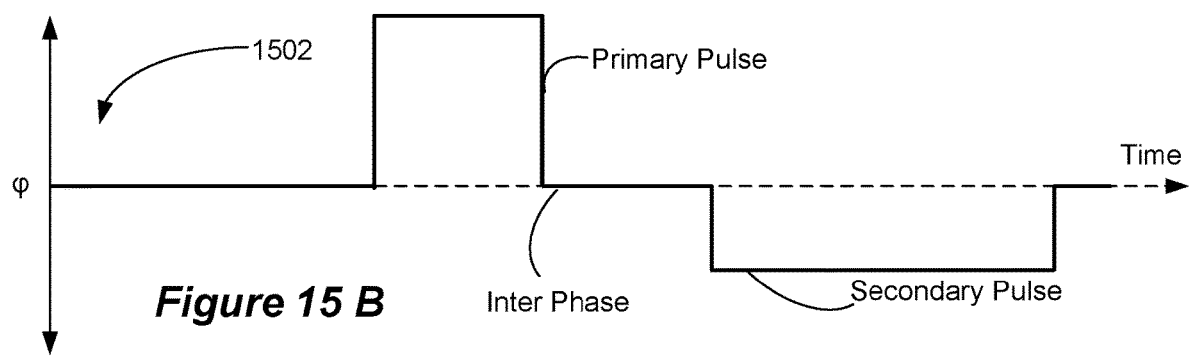
Figure 16:
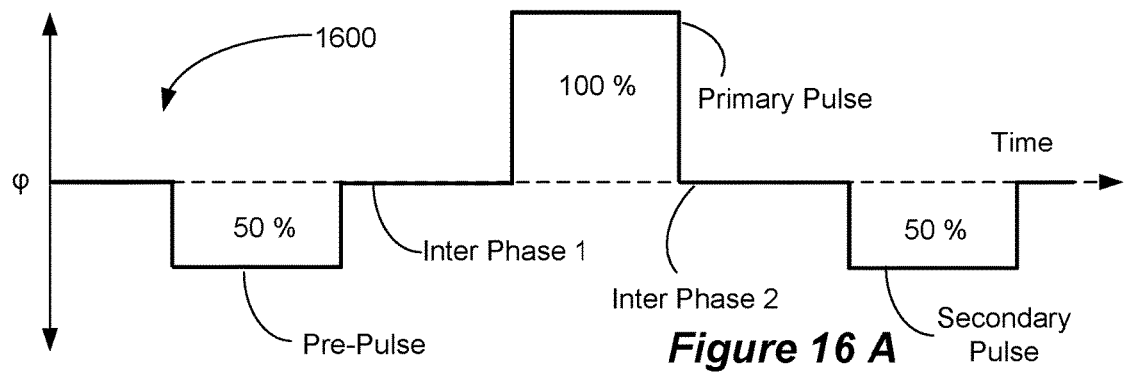
FIGS. 16A and 16B show adjustment of waveform phases.
Figure 16:
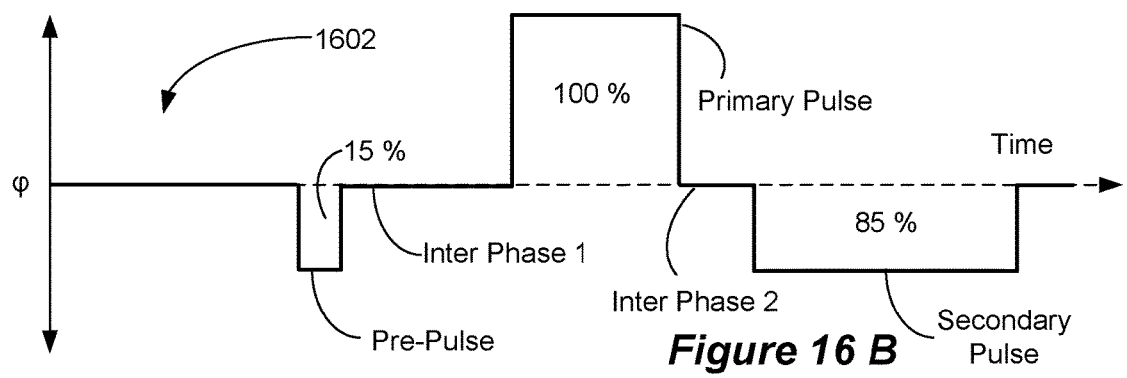

The waveform 1500 includes a primary pulse, a secondary pulse, and an inter-phase segment between the primary and secondary pulses. The waveform 1500 is charged balanced because the amount of charged passed during the primary pulse is the same as the charge passed during the secondary pulses (the area under the pulses is the same). Assume that the user wishes to modify the waveform 1500 to generate a waveform 1502 (FIG. 15B) according to the following constraints: (1) the waveform is to remain charge-balanced and (2) the amplitude of the secondary pulse is to be 50% the amplitude of the primary pulse. Clearly, the pulse width of the secondary pulse must be twice that of the primary pulse so that an equal amount of charge is passed during the two pulses, as shown in FIG. 15B.

Waveform 1600 (FIG. 16A) features a pre-pulse, a primary pulse, a secondary pulse, a first inter-phase segment (Inter Phase 1) between the pre-pulse and the primary pulse and a second inter-phase segment (Inter Phase 2) between the primary pulse and the secondary pulse. The waveform 1600 is charge balanced because the anodic charge passed during the primary pulse is equal to the cathodic charge passed during the combination of the pre-pulse and the secondary pulse. In waveform 1600, 50% of the charge passed in the anodic primary pulse is balanced by the cathodic pre-pulse and the other 50% of the anodic charge is balanced by the cathodic secondary pulse. In waveform 1602 (FIG. 16B), 15% of the charge passed in the anodic primary pulse is balanced by the cathodic pre-pulse and the other 85% of the anodic charge is balanced by the cathodic secondary pulse.

It is apparent from the discussion of the waveforms illustrated in FIGS. 15A, 15B, 16A, and 16B that parameters of the waveforms are interdependent. The methods and systems described herein allow a user to define (i.e., constrain) certain parameters of a waveform and the system automatically adjusts adjustable dependent parameters of the waveform, accordingly, to comply with the constraints. In the waveforms illustrated in FIGS. 15A and 15B, the constrained parameters are the pulse width of the primary pulse, charge balance, and the primary pulse/secondary pulse amplitude ratio. The adjustable dependent parameter is the pulse width (or total charge) of the secondary pulse, which can be adjusted automatically by the system. In the waveforms illustrated in FIGS. 16A and 16B, the defined parameters may be the ratio of charges balanced by the pre-pulse and secondary pulse and the amplitudes of the pulses. The system may adjust the pulse width of the pulses automatically. The pulse width of one or more of the pulse might be further defined, in which case, the system may adjust the pulse width of the undefined pulse width accordingly.

FIG. 17 illustrates an example of a workflow 1700 using the disclosed system. Initially, a user determines initial parameters of a waveform 1702. A user may use a user interface (GUI), as described in more detail below. The selection of initial parameters may include aspects of the waveform, such as the number phases (e.g., monophasic, biphasic, triphasic, etc.), the polarities of the segments of the pulse, the presence and duration of inter-phasic pulses, the amount of active and passive charge recovery. Other initial parameters will be apparent to a person of skill in the art.

The user can then constrain some of the parameters of the waveform 1704. For example, the user may define the pulse width of certain segments, the amplitudes or amplitude ratios of some of the pulses, the amount of charge balanced between phases of the waveform, etc. Based on the user defined constraints, the system adjusts adjustable parameters of the waveform 1706. FIG. 18 provides non-inclusive examples of parameters that may be defined and adjusted. Again, other examples will be apparent to a person of skill in the art.

It should be noted that the system may also include additional fail-safes or constraints that may prevent the user from deriving a waveform that may be problematic. For example, if an unsafe or intolerable amount of charge recovery would arise from a proposed waveform, the system may require further adjustment or definition of waveform parameters. Likewise, the system may be programmed to prevent a waveform that would be problematic because of energy usage, temperature, etc. The system may issue a warning or simply not allow such a waveform to be constructed.

Figure 19:
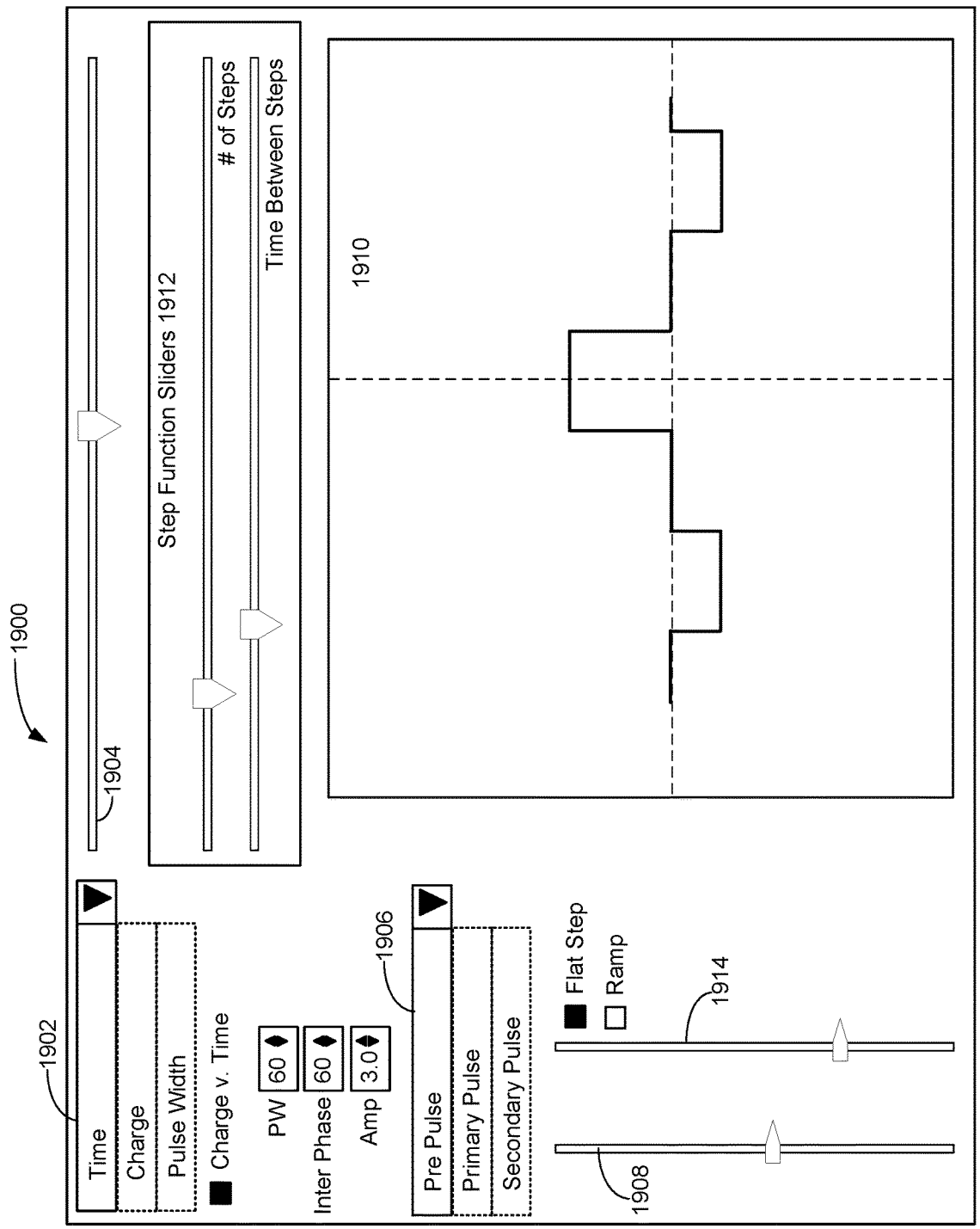
FIG. 19 shows a GUI for adjusting waveform parameters.

FIG. 19 illustrates an example of a GUI 1900 for controlling waveforms, as described above. The GUI 1900 includes slider bars and dropdown menus for controlling the function of the slider bars. For example, drop down menu 1902 can control the function of the slider bar 1904. The function of slider bar 1908 is controlled by "Charge vs Time" checkbox. Dropdown 1906 controls the function of slider bar 1914 and Step Function Sliders 1912. Using the dropdown menus and slider bars, the user can define parameters of the waveform as described above. The GUI 1900 can also include a display 1910, which can present a graphical representation of the waveform as it is created and modified. As described above, the system automatically adjusts adjustable parameters based on the user's adjustment of confined parameters. The adjustments by the user and system can be reflected in the waveform displayed on display 1910. It should be noted that values and ratios, etc., can be entered numerically, as well, and other graphical GUI elements, such as radio buttons can be used instead of, or in addition to dropdown menus.

Figure 20:
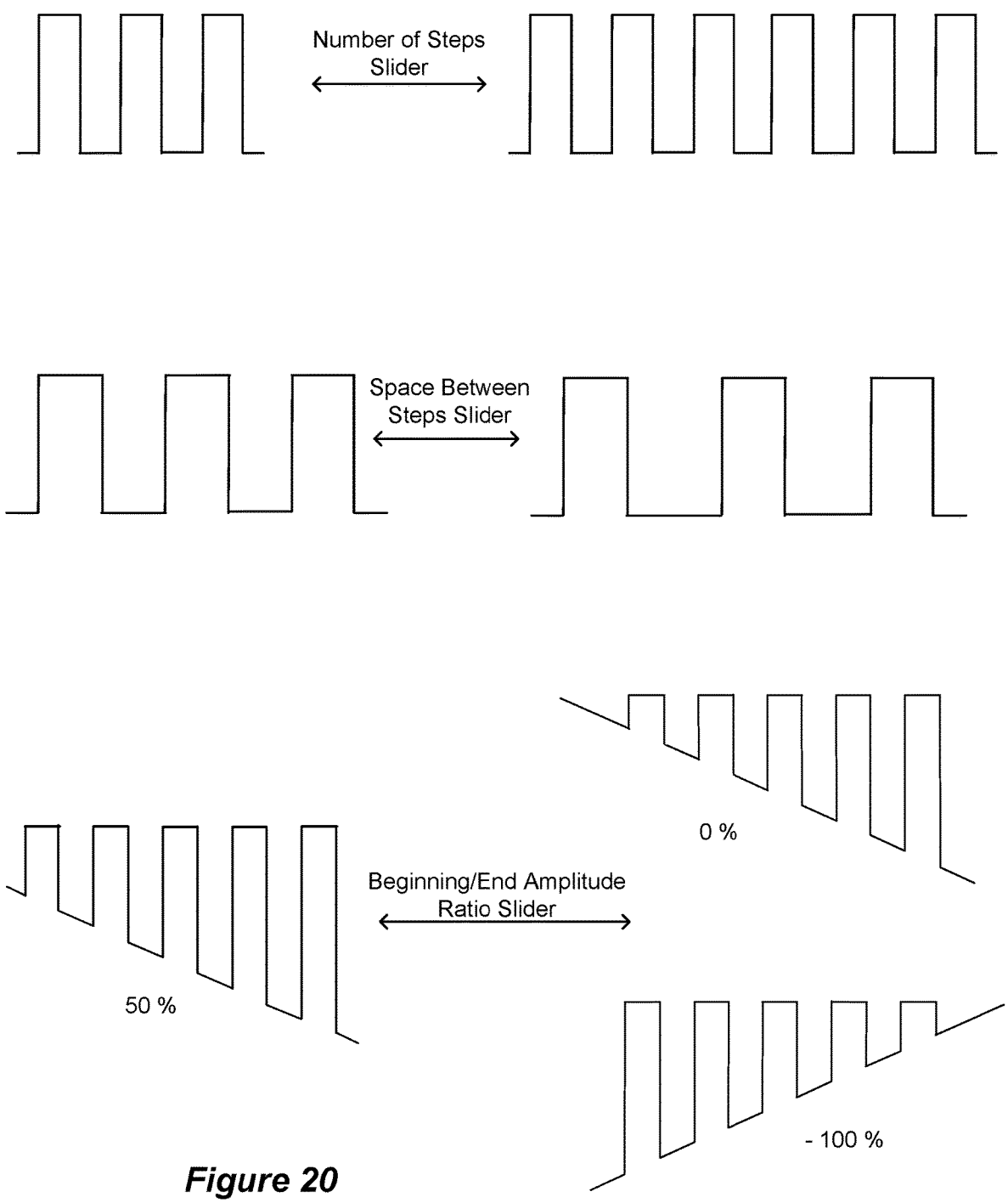
FIG. 20 shows waveform parameters adjustable using step sliders.

The GUI 1900 can also contain Step Function Sliders 1912 and 1914 for controlling parameters of step function (or multi-pulsed) waveforms. For example, sliders 1912 may be used to control the number of steps and the time between the steps, for example in the pre-pulse phase, as selected in dropdown menu 1906. Slider 1914 may be used to control ramping of the steps, for example, by controlling the ratio of amplitudes of the beginning and ending steps. Examples of how the step sliders are used are illustrated in FIG. 20.

Figure 21:
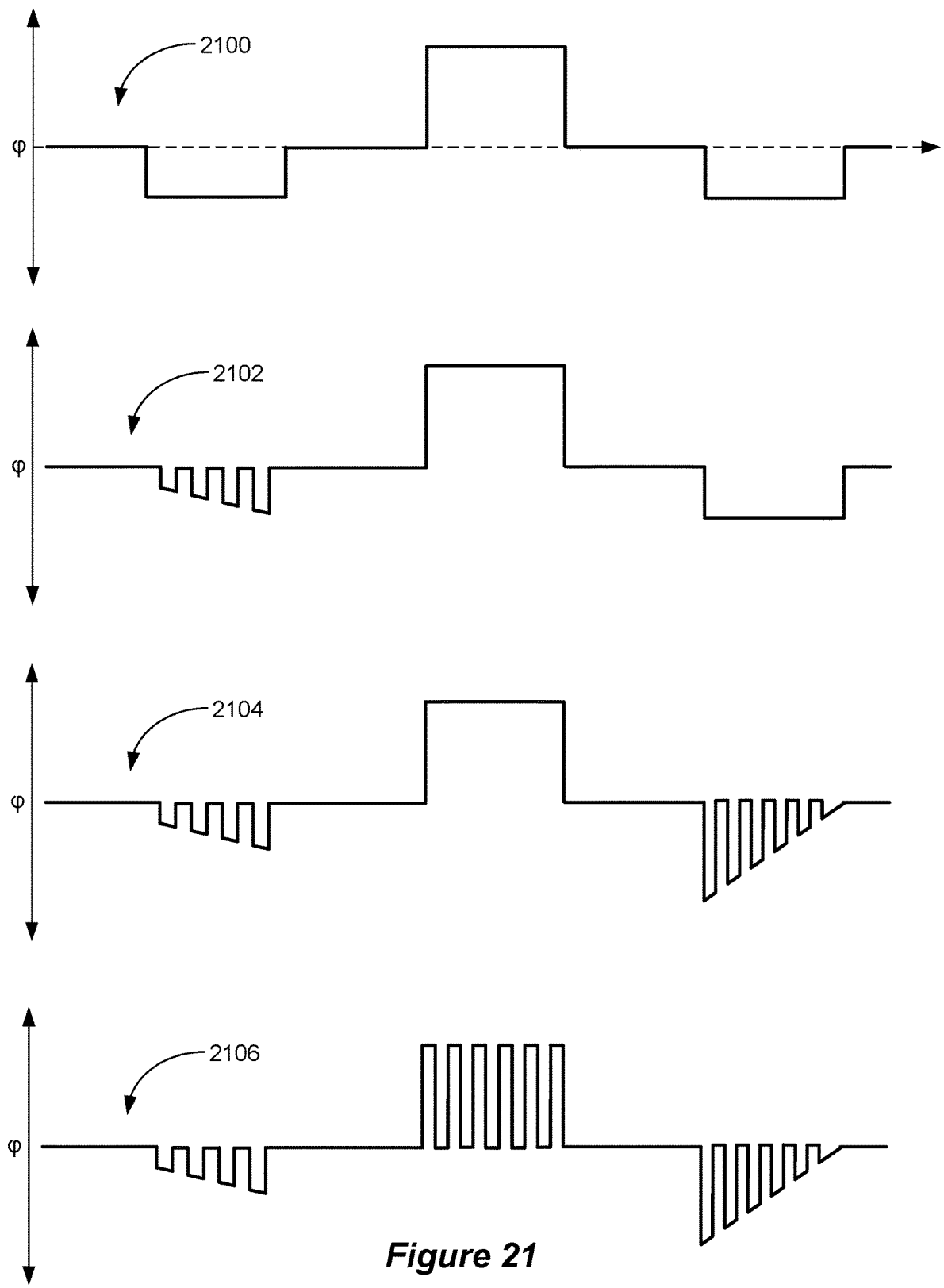
FIG. 21 shows the evolution of a waveform by adjusting waveform parameters.

FIG. 21 illustrates the generation of a complex waveform using the controls of GUI 1900. First a waveform 2100 is constructed by defining a pre-pulse, a primary pulse, and a secondary pulse, as described above. As explained above, the user may define certain parameters of the waveform, such as the relative amplitude ratios of the pulses, the pulse width or pulse width ratios of some of the pulses, etc., and the system will automatically adjust adjustable parameters accordingly. The user may apply the step slider functions of the GUI, for example, to adjust the pre-pulse component of the waveform, as illustrated in waveform 2102. Likewise, the step slider functions can be used to add stepping functions to the secondary pulse and primary pulse components, as illustrated in waveforms 2104 and 2106, respectively.

The GUI 1900 may include further controls that are not illustrated for composing waveforms. For example, in addition to the ramping/stepping functions, the GUI may include additional function controllers, such as Bezier function controllers, whereby a user can define control points, histograms, etc., for defining more complex waveform shapes.

Figure 22:
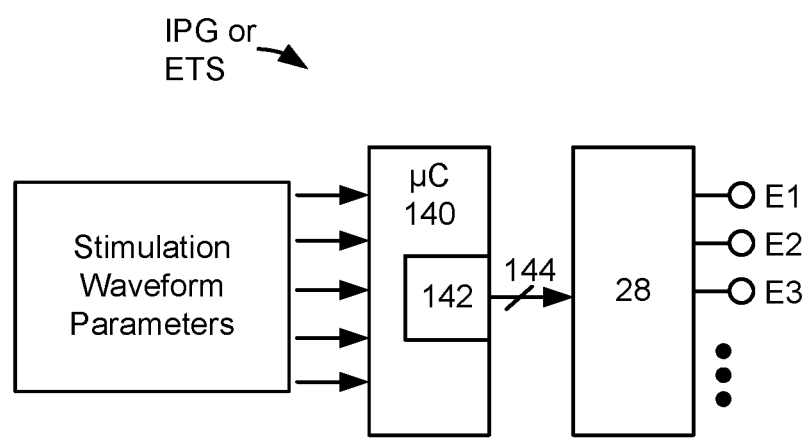
FIG. 22 shows aspects of an IPG or ETS capable of forming the pulses as specified by the GUI.

FIG. 22 shows an IPG or ETS capable of forming the pulses as specified by the GUIs described above. The stimulation waveform parameters entered from the GUI can be wirelessly transmitted by the external device 50 to an antenna in the IPG or ETS. The stimulation parameters, once wirelessly received, are provided to control circuitry 140. Control circuitry 140 may comprise a microcontroller for example, such as Part Number MSP430, manufactured by Texas Instruments, which is described in data sheets at www.ti.com. The control circuitry 140 more generally can comprise a microprocessor, Field Programmable Gate Array, Programmable Logic Device, Application Specific Integrated Circuit (ASIC), Digital Signal Processor or like devices. Control circuitry 140 may also be based on well-known ARM microcontroller technology. Control circuitry 140 may include a central processing unit capable of executing instructions, with such instructions stored in volatile or non-volatile memory within or associated with the control circuitry. Control circuitry 140 may also include, operate in conjunction with, or be embedded within an Application Specific Integrated Circuit (ASIC), such as described in U.S. Patent Application Publications 2008/0319497, 2012/0095529, 2018/0071513, or 2018/0071520, which are incorporated herein by reference. The control circuitry 140 may comprise an integrated circuit with a monocrystalline substrate, or may comprise any number of such integrated circuits operating as a system. Control circuitry may also be included as part of a System-on-Chip (SoC) or a System-on-Module (SoM) which may incorporate memory devices and other digital interfaces.

In FIG. 22, the control circuitry 140 includes pulse logic 142, which receives the stimulation parameters and forms various control signals 144 for the stimulation circuitry 28. Such control signals 144 specify the timing and polarity of the stimulation pulses appearing at each of the selected electrodes, as well as the amplitude of the current each selected electrode will provide.

Aspects of the disclosure provide algorithms for providing waveforms for neuromodulation and GUI(s) for selecting and tailoring such waveforms. Aspects of the algorithms and GUI(s) may be embodied within an IPG (or ETS) and/or within one or more external devices such as a clinician programmer or external controller. One of skill in the art will understand that the particulars of the algorithms and of the GUI(s) may depend on where they are executed and may depend on selections the clinician or patient has previously made. Instructions for the algorithms and/or GUI(s) can be stored on a non-transitory computer readable media, such as a solid state, optical, or magnetic memory, and operable within the control circuitry of the relevant external device.

Although particular embodiments have been shown and described, the above discussion should not limit the present invention to these embodiments. Various changes and modifications may be made without departing from the spirit and scope of the present invention. Thus, the present invention is intended to cover equivalent embodiments that may fall within the scope of the present invention as defined by the claims.

What is claimed is:

1. An apparatus for providing stimulation to a patient implanted with one or more electrode leads comprising a plurality of electrodes, wherein the apparatus selectively stimulates target neural elements and avoids activating non-target neural elements, the apparatus comprising:

control circuitry configured to cause one or more of the electrodes to provide a stimulation waveform, wherein the stimulation waveform comprises:
at least one stimulation phase and one or more of at least one pre-pulse phase or one post-pulse phase,
wherein the at least one pre-pulse phase or at least one post-pulse phase has an amplitude programmed to change from an initial first amplitude to at least a second amplitude over a duration of the pre-pulse phase or post-pulse phase,
wherein the initial first amplitude is below an initial activation threshold of the non-target neural elements and the second amplitude is above the initial activation threshold of the non-target neural elements, and
wherein at least a part of the at least one pre-pulse phase or at least one post-pulse phase is opposite polarity than the at least one stimulation phase.

2. The apparatus of claim 1, wherein the amplitude is programmed to ramp between the initial first amplitude and the second amplitude over the duration.

3. The apparatus of claim 1, wherein the amplitude is programmed to step from the initial first amplitude to the second amplitude during the duration.

4. The apparatus of claim 1, wherein the non-target neural elements are selected from neuronal cells and fibers of passage.

5. The apparatus of claim 1, wherein the apparatus is an implantable pulse generator (IPG).

6. The apparatus of claim 1, wherein the apparatus is a clinician programmer.

7. The apparatus of claim 1, wherein the apparatus is an external controller.

8. The apparatus of claim 1, wherein the control circuitry is configured to determine the initial activation amplitude of the non-target neural elements.

9. A method of preferentially stimulating target neural elements and avoiding activating non-target neural elements, the method comprising:
applying a stimulation waveform to a tissue comprising the target neural elements and non-target neural elements, wherein
the stimulation waveform comprises:
at least one stimulation phase, and one or more of at least one pre-pulse phase or one post-pulse phase, wherein
the at least one pre-pulse phase or at least one post-pulse phase has an amplitude programmed to change from an initial first amplitude to at least a second amplitude over a duration of the pre-pulse phase or post-pulse phase, wherein
the initial first amplitude is below an initial activation threshold of the non-target neural elements and the second amplitude is above the initial activation threshold of the non-target neural elements, and wherein
at least a part of the at least one pre-pulse phase or the at least one post-pulse phase is opposite polarity than the at least one stimulation phase.

10. The method of claim 9, wherein the amplitude is programmed to ramp between the initial first amplitude and the second amplitude.

11. The method of claim 9, wherein the amplitude is programmed to step between the initial first amplitude and the second amplitude.

12. The method of claim 9, further comprising determining the initial activation threshold of the non-target neural elements.

13. The method of claim 9, wherein the non-target neural elements are neuronal cells.

14. The method of claim 9, wherein the non-target neural elements are fibers of passage.

* * * * *